United States Patent [19]

Haas et al.

[11] Patent Number: 5,663,362

[45] Date of Patent: *Sep. 2, 1997

[54] SUBSTITUTED TRIAZOLINONES

[75] Inventors: Wilhelm Haas, Pulheim; Karl-Heinz Linker, Leverkusen; Otto Schallner, Monheim; Kurt Findeisen, Leverkusen; Hans-Joachim Santel, Leverkusen; Markus Dollinger, Leichlingen, all of Germany

[73] Assignee: Bayer Aktiengesellschaft, Leverkusen, Germany

[*] Notice: The term of this patent shall not extend beyond the expiration date of Pat. No. 5,378,687.

[21] Appl. No.: 469,250

[22] Filed: Jun. 6, 1995

Related U.S. Application Data

[62] Division of Ser. No. 189,017, Jan. 28, 1994, Pat. No. 5,464,810.

[30] Foreign Application Priority Data

Feb. 5, 1993 [DE] Germany .................. 43 03 376.8

[51] Int. Cl.$^6$ ............................................ C07D 249/12
[52] U.S. Cl. ................... 548/263.2; 548/263.4; 548/263.8; 548/264.4; 548/110
[58] Field of Search .................. 548/263.2, 263.4, 548/263.8, 264.4, 110

[56] References Cited

U.S. PATENT DOCUMENTS 5,378,681  1/1995  Schallner et al. .......... 504/273

FOREIGN PATENT DOCUMENTS 2230261  10/1990  United Kingdom .
WO8703782  7/1987  WIPO .

OTHER PUBLICATIONS

Chemical Abstracts, vol. 118, 1993, p. 850; CA# 168823z: "Preparation of 2-(4-hydroxyphenoxy)propionic acid dicyclohexylamine salt", M. Hashimoto.

Primary Examiner—Patricia L. Morris
Attorney, Agent, or Firm—Sprung Horn Kramer & Woods

[57] ABSTRACT

The invention relates to novel substituted triazolinones of the general formula (I),

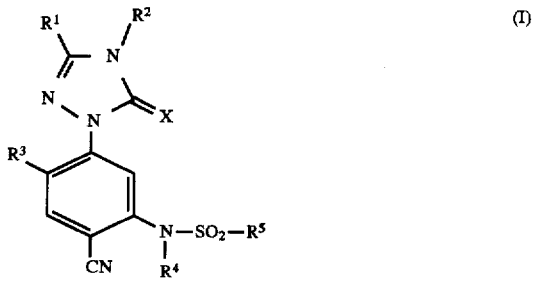

in which $R^1$ represents hydrogen, halogen, cyano, hydroxyl or one of the radicals —$R^6$, —O—$R^6$, —O—$NR^6R^7$, —S—$R^6$, —S(O)—$R^6$ or —$SO_2$—$R^6$, $R^2$ represents hydrogen, hydroxyl, amino, cyano or one of the radicals —$R^6$, —O—$R^6$ or —N=$CR^6R^7$, $R^3$ represents hydrogen, halogen, alkyl or halogenoalkyl, $R^4$ represents hydrogen, one of the radicals —$R^6$, —O—$R^6$ or —SO—$R^6$ or an inorganic or organic cation and $R^5$ represents amino, hydroxyl or one of the radicals —$R^6$ or —$NR^6R^7$, or $R^4$ and $R^5$ together represent a divalent alkanediyl radical and X represents oxygen or sulphur, where $R^6$ represents alkyl, alkenyl, alkinyl, cycloalkyl, aryl or heterocyclyl, which may each optionally be substituted, $R^7$ represents hydrogen or represents alkyl, alkenyl, alkinyl, cycloalkyl or aryl, which may each optionally be substituted, processes for their preparation, novel intermediates and their use as herbicides.

5 Claims, No Drawings

SUBSTITUTED TRIAZOLINONES

This is a division of application Ser. No. 08/189,017, filed on Jan. 28, 1994 now U.S. Pat. No. 5,464,810.

The invention relates to novel substituted triazolinones, processes for their preparation and their use as herbicides.

It is known that certain substituted triazolinones, such as for example the compound 3-methyl-4-propargyl-1-(2,5-difluoro-4-cyano-phenyl)-1,2,4-triazolin-5-one, possess herbicidal properties (see for example, DE 38 39 480).

However, the herbicidal activity of these previously known compounds against problem weeds is, like their tolerance by important cultivated plants, not completely satisfactory in all application areas.

Novel substituted triazolinones of the general formula (I),

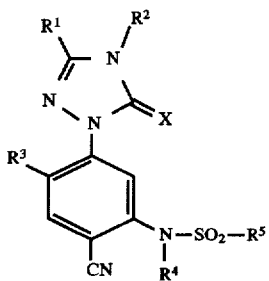

in which

R$^1$ represents hydrogen, halogen, cyano, hydroxyl or one of the radicals —R$^6$, —O—R$^6$, —O—NR$^6$R$^7$, —S—R$^6$, —S(O)—R$^6$ or —SO$_2$—R$^6$, R$^2$ represents hydrogen, hydroxyl, amino, cyano or one of the radicals —R$^6$, —O—R$^6$ or —N=CR$^6$R$^7$, R$^3$ represents hydrogen, halogen, alkyl or halogenoalkyl, R$^4$ represents hydrogen, one of the radicals —R$^6$, —O—R$^6$ or —SO$_2$—R$^6$ or an inorganic or organic cation and R$^5$ represents amino, hydroxyl or one of the radicals —R$^6$ or —NR$^6$R$^7$, or R$^4$ and R$^5$ together represent a divalent alkanediyl radical and X represents oxygen or sulphur, where R$^6$ represents alkyl, alkenyl, alkinyl, cycloalkyl, aryl or heterocyclyl, which may each optionally be substituted, and R$^7$ represents hydrogen or represents alkyl, alkenyl, alkinyl, cycloalkyl or aryl, which may each optionally be substituted, have now been found.

Depending on the type of substituents, the compounds of the formula (I) may optionally be present as geometric and/or optical isomers or as isomer mixtures of different compositions. Both the pure isomers and the isomer mixtures are claimed according to the invention.

It has furthermore been found that the novel substituted triazolinones of the general formula (I),

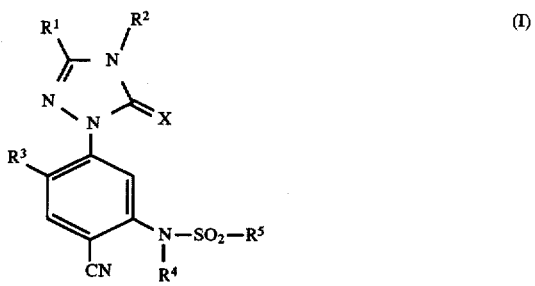

in which

R$^1$ represents hydrogen, halogen, cyano, hydroxyl or one of the radicals —R$^6$, —O—R$^6$, —O—NR$^6$R$^7$, —S—R$^6$, —S(O)—R$^6$ or —SO$_2$—R$^6$, R$^2$ represents hydrogen, hydroxyl, amino, cyano or one of the radicals —R$^6$, —O—R$^6$ or —N=CR$^6$R$^7$, R$^3$ represents hydrogen, halogen, alkyl or halogenoalkyl, R$^4$ represents hydrogen, one of the radicals —R$^6$, —O—R$^6$ or —SO$_2$—R$^6$ or an inorganic or organic cation and R$^5$ represents amino, hydroxyl or one of the radicals —R$^6$ or —NR$^6$R$^7$, or R$^4$ and R$^5$ together represent a divalent alkanediyl radical and X represents oxygen or sulphur, where R$^6$ represents alkyl, alkenyl, alkinyl, cycloalkyl, aryl or heterocyclyl, which may each optionally be substituted, and R$^7$ represents hydrogen or represents alkyl, alkenyl, alkinyl, cycloalkyl or aryl, which may each optionally be substituted, are obtained, when a) 1H-triazolinones of the formula (II),

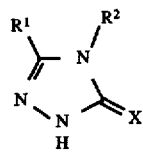

in which

R$^1$, R$^2$ and X have the above meanings, are reacted with halogenobenzene derivatives of the formula (III),

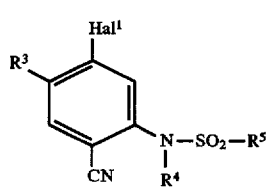

in which

R$^3$, R$^4$ and R$^5$ have the above meanings and

Hal$^1$ represents halogen, in particular fluorine, chlorine, bromine and iodine, optionally in the presence of a diluent and optionally in the presence of a reaction aid, or when b) substituted triazolinones of the formula (IV),

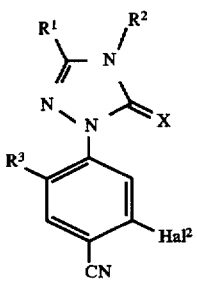

in which
R$^1$, R$^2$, R$^3$ and X have the above meanings and
Hal$^2$ represents halogen,
are reacted with sulphonamides of the formula (V),

    (V)

in which
R$^4$ and R$^5$ have the above meanings,
optionally in the presence of a diluent and optionally in the presence of a reaction aid, or when c) substituted triazolinones of the formula (Ia),

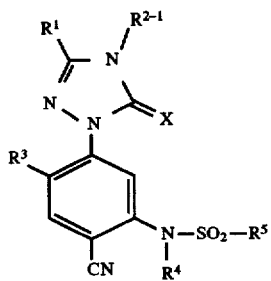    (Ia)

in which
R$^1$, R$^3$, R$^4$, R$^5$ and X have the above meanings and
R$^{2-1}$ represents amino, are reacted with sodium nitrite in the presence of an acid and optionally in the presence of a diluent, or when d) substituted triazolinones of the formula (Ib),

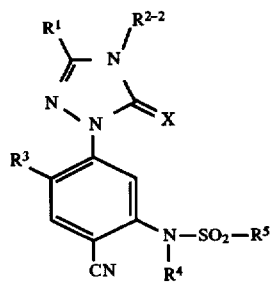    (Ib)

in which
R$^1$, R$^3$, R$^4$, R$^5$ and X have the above meanings and
R$^{2-2}$ represents hydrogen,
are reacted with alkylating agents of the formula (VI),

    (VI)

in which
R$^{2-3}$ represents alkyl, alkenyl, alkinyl or cycloalkyl, which may each optionally be substituted, and
E$^1$ represents an electron-attracting leaving group, optionally in the presence of a diluent and optionally in the presence of a reaction aid, or when e) substituted triazolinones of the formula (Ic),

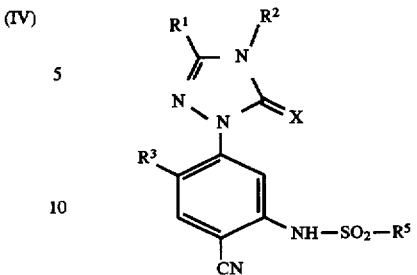    (Ic)

in which
R$^1$, R$^2$, R$^3$, R$^5$ and X have the above meanings, are reacted with alkylating agents of the formula (VII),

    (VII)

in which
R$^{4-1}$ represents alkyl, alkenyl, alkinyl, halogenoalkyl, halogenoalkenyl, halogenoalkinyl, alkoxyalkyl or optionally substituted cycloalkyl and
E$^2$ represents an electron-attracting leaving group, optionally in the presence of a diluent and optionally in the presence of a reaction aid, or when f) substituted triazolinones of the formula (VIII),

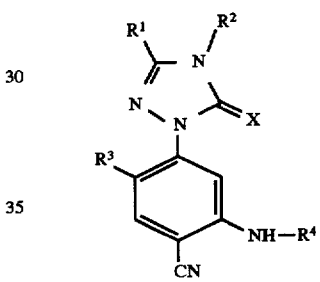    (VIII)

in which
R$^1$, R$^2$, R$^3$, R$^4$ and X have the above meanings, are reacted with sulphonyl halides of the formula (IX),

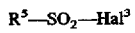    (IX)

in which
R$^5$ has the above meaning and
Hal$^3$ represents halogen,
optionally in the presence of a diluent and optionally in the presence of a reaction aid.

Finally, it has been found that the novel substituted triazolinones of the general formula (I) possess herbicidal properties.

Surprisingly, the substituted triazolinones of the general formula (I) according to the invention show a considerably improved herbicidal activity against problem weeds and at the same time an improved tolerance by useful plants when compared with the substituted triazolinones known from the prior art, such as, for example, the compound 3-methyl-4-propargyl-1-(2,5-difluoro-4-cyano-phenyl)-1,2,4-triazolin-5-one, which are compounds related chemically and in terms of activity.

The substituted triazolinones of the invention are generally defined by the formula (I). Preferred compounds of the formula (I) are those in which R$^1$ represents hydrogen, fluorine, chlorine, bromine, iodine, cyano, hydroxyl or one of the radicals —R$^6$, —O—R$^6$, —O—NR$^6$R$^7$, —S—R$^6$, —S(O)—R$^6$ or —SO$_2$—R$^6$, $R^2$ represents hydrogen, hydroxyl, amino, cyano or one of the radicals —$R^6$, —O—$R^6$ or —N=$CR^6R^7$, $R^3$ represents hydrogen, fluorine, chlorine, bromine, iodine, a straight chain or branched alkyl having from 1 to 8 carbon atoms or a straight chain or branched halogenoalkyl having from 1 to 8 carbon atoms and from 1 to 17 halogen atoms which may be identical or different—in particular fluorine, chlorine, bromine or iodine—, $R^4$ represents hydrogen, one of the radicals —$R^6$, —O—$R^6$ or —$SO_2$—$R^6$, one equivalent of an alkali metal or alkaline earth metal cation, or an ammonium cation which may optionally be singly or multiply substituted by alkyl having from 1 to 16 carbon atoms and which may be identical or different, and $R^5$ represents amino, hydroxyl or one of the radicals —$R^6$ or —$NR^6R^7$, or $R^4$ and $R^5$ together represent a divalent alkanediyl radical having from 2 to 7 carbon atoms and X represents oxygen or sulphur, where $R^6$ represents straight chain or branched alkyl having from 1 to 14 carbon atoms and which may optionally be singly or multiply substituted by substituents which may be identical or different, possible substituents being:

halogen—in particular fluorine, chlorine, bromine and/or iodine—, cyano, carboxyl, carbamoyl, or alkoxy, alkoxyalkoxy, alkylthio, alkylsulphinyl, alkylsulphonyl, alkoxycarbonyl, N-alkylaminocarbonyl, N,N-dialkylaminocarbonyl, trialkylsilyl or alkylsulphonylaminocarbonyl which may each be straight chain or branched and each have from 1 to 8 carbon atoms in the individual alkyl moieties, or heterocyclyl, where the hetero cyclyl radical is afrom five- to seven-membered, optionally benzo-fused, saturated or unsaturated heterocycle having from 1 to 3 hetero-atoms which may be identical or different—in particular nitrogen, oxygen and/or sulphur—;

$R^6$ also represents alkenyl or alkinyl each having from 2 to 8 carbon atoms and which may each optionally be singly or multiply substituted by halogen which may be identical or different—in particular fluorine, chlorine, bromine and/or iodine;

$R^6$ also represents cycloalkyl having from 3 to 7 carbon atoms and which may optionally be singly or multiply substituted by halogen which may be identical or different—in particular fluorine, chlorine, bromine and/or iodine—and/or straight chain or branched alkyl having from 1 to 4 carbon atoms;

$R^6$ also represents arylalkyl or aryl each having from 6 to 10 carbon atoms in the aryl part and optionally from 1 to 4 carbon atoms in the straight chain or branched alkyl part and which may each optionally be singly or multiply substituted in the aryl part by substituents which are identical or different, or a saturated or unsaturated, from five- to seven- membered heterocyclyl radical having from 1 to 3 heteroatoms which may be identical or different—in particular nitrogen, oxygen and/or sulphur—and which may optionally be singly or multiply substituted by substituents which may be identical or different, and/or be benzofused, possible aryl and heterocyclyl substituents in each case being:

halogen, cyano, nitro, amino, N-acetylamino, or alkyl, alkoxy, alkylthio, alkylsulphinyl or alkylsulphonyl which may each be straight chain or branched and each have from 1 to 6 carbon atoms, halogenoalkyl, halogenoalkoxy, halogenoalkylthio, halogenoalkylsulphinyl or halogenoalkylsulphonyl which may each be straight chain or branched and each have from 1 to 6 carbon atoms and from 1 to 13 halogen atoms which may be identical or different, alkoxycarbonyl or alkoximinoalkyl which may each be straight chain or branched and each have from 1 to 6 carbon atoms in the individual alkyl parts and substituted phenyl which may optionally be singly or multiply substituted by substituents which may be identical or different and comprise halogen and/or straight chain or branched alkyl or alkoxy each having from 1 to 6 carbon atoms and/or straight chain or branched halogenoalkyl or halogenoalkoxy each having from 1 to 6 carbon atoms and from 1 to 13 halogen atoms which may be identical or different;

$R^7$ represents hydrogen or straight chain or branched alkyl having from 1 to 8 carbon atoms and which may optionally be singly or multiply substituted by substituents which may be identical or different, possible substituents being:

halogen—in particular fluorine, chlorine, bromine and/or iodine—, cyano, carboxyl, carbamoyl, or alkoxy, alkoxyalkoxy, alkylthio, alkylsulphinyl, alkylsulphonyl, alkoxycarbonyl, N-alkylaminocarbonyl, N,N-dialkylaminocarbonyl, trialkylsilyl or alkylsulphonylaminocarbonyl which may each be straight chain or branched and each have from 1 to 8 carbon atoms in the individual alkyl moieties, or heterocyclyl, where the heterocyclyl radical represents a from five- to seven-membered, optionally benzo-fused, saturated or unsaturated heterocycle having from 1 to 3 heteroatoms which may be same or different—in particular nitrogen, oxygen and/or sulphur—;

$R^7$ also represents alkenyl or alkinyl each having from 2 to 8 carbon atoms and which may each optionally be singly or multiply substituted by halogen which may be identical or different—in particular fluorine, chlorine, bromine and/or iodine;

$R^7$ also represents cycloalkyl having from 3 to 7 carbon atoms and which may optionally be singly or multiply substituted by halogen which may be identical or different—in particular fluorine, chlorine, bromine and/ or iodine—and/or straight chain or branched alkyl having from 1 to 4 carbon atoms; or $R^7$ represents arylalkyl or aryl each having from 6 to 10 carbon atoms in the aryl part and optionally from 1 to 4 carbon atoms in the straight chain or branched alkyl part and which may each optionally be singly or multiply substituted in the aryl part by substituents which may be identical or different, possible aryl substituents being:

halogen, cyano, nitro, or alkyl, alkoxy, alkylthio, alkylsulphinyl or alkylsulphonyl which may each be straight chain or branched and each have from 1 to 6 carbon atoms, halogenoalkyl, halogenoalkoxy, halogenoalkylthio, halogenoalkylsulphinyl or halogenoalkylsulphonyl which may each be straight chain or branched and each have from 1 to 6 carbon atoms and from 1 to 13 halogen atoms which may be identical or different, alkoxycarbonyl or alkoximinoalkyl which may each be straight chain or branched and each have from 1 to 6 carbon atoms in the individual alkyl parts and substituted phenyl which may optionally be singly or multiply substituted by substituents which may be identical or different and comprise halogen and/or straight chain or branched alkyl or alkoxy each having from 1 to 6 carbon atoms and/or straight chain or branched halogenoalkyl or halogenoalkoxy each having from 1 to 6 carbon atoms and from 1 to 13 halogen atoms which may be identical or different.

Particularly preferred compounds of the formula (I) are those in which $R^1$ represents hydrogen, fluorine, chlorine, bromine, cyano, hydroxyl or one of the radicals $-R^6$, $-O-R^6$, $-O-NR^6R^7$, $-S-R^6$, $-S(O)-R^6$ or $-SO_2-R^6$, $R^2$ represents hydrogen, hydroxyl, amino, cyano or one of the radicals $-R^6$, $-O-R^6$ or $-N=CR^6R^7$, $R^3$ represents hydrogen, fluorine, chlorine, bromine, a straight chain or branched alkyl having from 1 to 6 carbon atoms or a straight chain or branched halogenoalkyl having from 1 to 6 carbon atoms and from 1 to 13 halogen atoms which my be identical or different—in particular fluorine, chlorine or bromine, $R^4$ represents hydrogen, one of the radicals $-R^6$, $-O-R^6$ or $-SO_2-R^6$, one equivalent of an alkali metal oralkaline earth metal cation or an ammonium cation which may optionally be singiy or multiply substituted by alkyl having from 1 to 12 carbon atoms and which may be identical or different, and $R^5$ represents amino, hydroxyl or one of the radicals $-R^6$ or $-NR^6R^7$, or $R^4$ and $R^5$ together represent a divalent alkanediyl radical having from 2 to 6 carbon atoms and X represents oxygen or sulphur, where $R^6$ represents straight chain or branched alkyl having from 1 to 12 carbon atoms and which may optionally be monosubstituted, possible substituents being:

cyano, carboxyl, carbamoyl, or alkoxy, alkoxyalkoxy, alkylthio, alkylsulphinyl, alkylsulphonyl, alkoxycarbonyl, N-alkylaminocarbonyl, N,N-dialkylaminocarbonyl, trialkylsilyl or alkylsulphonylaminocarbonyl which may each be straight chain or branched and each have from 1 to 6 carbon atoms in the individual alkyl moieties, or heterocyclyl, where the heterocyclyl radical is a five- or six-membered, saturated or unsaturated heterocycle having from 1 to 3 heteroatoms which may be identical or different—in particular nitrogen, oxygen and/or sulphur—;

$R^6$ also represents a straight chain or branched halogenoalkyl having from 1 to 4 carbon atoms and from 1 to 9 halogen atoms which may be identical or different—in particular fluorine, chlorine or bromine—;

$R^6$ also represents alkenyl or alkinyl each having from 2 to 6 carbon atoms and which may each optionally be mono- to trisubstituted by halogen which may be identical or different—in particular fluorine, chlorine or bromine—;

$R^6$ also represents cycloalkyl having from 3 to 6 carbon atoms and which may optionally be mono- to tetrasubstituted by halogen which may be identical or different—in particular fluorine, chlorine or bromine—and/or straight chain or branched alkyl having from 1 to 3 carbon atoms;

$R^6$ also represents phenylalkyl or phenyl optionally having from 1 to 3 carbon atoms in the straight chain or branched alkyl part and which may each optionally be mono- to trisubstituted in the phenyl part by substituents which are identical or different, or a saturated or unsaturated, from five- to six-membered heteroaryl radical having from 1 to 3 heteroatoms which may be identical or different—in particular nitrogen, oxygen and/or sulphur—and which may optionally be mono- to trisubstituted by substituents which may be identical or different, and/or be benzofused, possible phenyl and heterocyclyl substituents in each case being:

halogen, cyano, nitro, amino, N-acetylamino, or alkyl, alkoxy, alkylthio, alkylsulphinyl or alkylsulphonyl which may each be straight chain or branched and each have from 1 to 4 carbon atoms, halogenoalkyl, halogenoalkoxy, halogenoalkylthio, halogenoalkylsulphinyl or halogenoalkylsulphonyl which may each be straight chain or branched and each have from 1 to 4 carbon atoms and from 1 to 9 halogen atoms which may be identical ordifferent, alkoxycarbonyl or alkoximinoalkyl which may each be straight chain or branched and each have from 1 to 4 carbon atoms in the individual alkyl parts and substituted phenyl which may optionally be singly or multiply substituted by substituents which may be identical or different and comprise halogen and/or straight chain or branched alkyl or alkoxy each having from 1 to 4 carbon atoms and/or straight chain or branched halogenoalkyl or halogenoalkoxy each having from 1 to 4 carbon atoms and from 1 to 9 halogen atoms which may be identical or different;

$R^7$ represents hydrogen for straight chain or branched alkyl having from 1 to 6 carbon atoms which may optionally be monosubstituted, possible substituents being:

cyano, carboxyl, carbamoyl, or alkoxy, alkoxyalkoxy, alkylthio, alkylsulphinyl, alkylsulphonyl, alkoxycarbonyl, N-alkylaminocarbonyl, N,N-dialkylaminocarbonyl, trialkylsilyl or alkylsulphonylaminocarbonyl which may each be straight chain or branched and each have from 1 to 6 carbon atoms in the individual alkyl moieties, or heterocyclyl, where the heterocyclyl radical represents a five- to seven-membered, saturated or unsaturated heterocycle having from 1 to 3 heteroatoms which may be identical or different—in particular nitrogen, oxygen and/or sulphur—;

$R^7$ also represents straight chain or branched halogenoalkyl having from 1 to 4 carbon atoms and from 1 to 9 halogen atoms whichmay be identical or different—in particular fluorine, chlorine or bromine—;

$R^7$ also represents alkenyl or alkinyl each having from 2 to 6 carbon atoms and which may each optionally be mono- to trisubstituted by halogen which may be identical or different in particular fluorine, chlorine or bromine;

$R^7$ also represents cycloalkyl having from 3 to 6 carbon atoms and which may optionally be mono- to tetrasubstituted by halogen which may be identical or different—in particular fluorine, chlorine or bromine—and/or straight chain or branched alkyl having from 1 to 3 carbon atoms; or $R^7$ represents phenylalkyl or phenyl optionally having from 1 to 3 carbon atoms in the straight chain or branched alkyl part and which may each optionally be mono- to trisubstituted in the phenyl part by substituents which may be identical or different, possible phenyl substituents in each case being:

fluorine, chlorine, bromine, iodine, cyano, nitro, or alkyl, alkoxy, alkylthio, alkylsulphinyl or alkylsulphonyl which may each be straight chain or branched and each have from 1 to 4 carbon atoms, halogenoalkyl, halogenoalkoxy, halogenoalkylthio, halogenoalkylsulphinyl or halogenoalkylsulphonyl which may each be straight chain or branched and each have from 1 to 4 carbon atoms and from 1 to 9 halogen atoms which may be identical or different, alkoxycarbonyl or alkoximinoalkyl which may each be straight chain or branched and each have from 1 to 4 carbon atoms in the individual alkyl parts and substituted phenyl which may optionally be singly or multiply substituted by substituents which may be identical or different and comprise halogen and/or straight chain or branched alkyl or alkoxy each having from 1 to 4 carbon atoms and/or straight chain or branched halogenoalkyl or halogenoalkoxy each having from 1 to 4 carbon atoms and from 1 to 9 halogen atoms which may be identical or different.

Most particularly preferred are compounds of the formula (I), in which $R^1$ represents hydrogen, fluorine, chlorine, bromine, cyano, hydroxyl or one of the radicals —$R^6$, —O—$R^6$, —O—$NR^6R^7$, —S—$R^6$, —S(O)—$R^6$ or —$SO_2$—$R^6$, $R^2$ represents hydrogen, hydroxyl, amino, cyano or one of the radicals —$R^6$, —O—$R^6$ or —N=$CR^6R^7$, $R^3$ represents hydrogen, fluorine, chlorine, bromine, a straight chain or branched alkyl having from 1 to 4 carbon atoms or a halogenoalkyl having from 1 to 2 carbon atoms and from 1 to 5 halogen atoms which may be identical or different—in particular fluorine, chlorine or bromine, $R^4$ represents hydrogen, one of the radicals —$R^6$, —O—$R^6$ or —$SO_2$—$R^6$, one equivalent of a sodium or potassium cation or an ammonium cation which my optionally be mono- to tetrasubstituted by alkyl having from 1 to 8 carbon atoms and which may be identical or different, and represents amino, hydroxyl or one of the radicals —$R^6$ or —$NR^6R^7$, or $R^4$ and $R^5$ together represent a divalent alkanediyl radical having from 2 to 5 carbon atoms and X represents oxygen or sulphur, where $R^6$ represents straight chain or branched alkyl having from 1 to 10 carbon atoms and which may optionally be monosubstituted, possible substituents being:

cyano, carboxyl, carbamoyl, or alkoxy, alkoxyalkoxy, alkylthio, alkylsulphinyl, alkylsulphonyl, alkoxycarbonyl, N-alkylaminocarbonyl, N,N-dialkylaminocarbonyl, trialkylsilyl or alkylsulphonylaminocarbonyl which may each be straight chain or branched and each have from 1 to 4 carbon atoms in the individual alkyl moieties, or heterocyclyl, where the heterocyclyl radical represents a five- or six-membered, saturated or unsaturated heterocycle having from 1 to 3 heteroatoms which may be identical or different—in particular nitrogen, oxygen and/or sulphur—;

$R^6$ also represents halogenoalkyl having 1 or 2 carbon atoms and from 1 to 5 halogen atoms which may be identical or different—in particular fluorine or chlorine—;

$R^6$ also represents alkenyl or alkinyl each having from 2 to 5 carbon atoms and which may each optionally be monosubstituted by halogen—in particular fluorine or chlorine;

$R^6$ also represents cyclopropyl which may optionally be mono- or disubstituted by substituents which may be identical or different and comprise fluorine, chlorine, methyl and/or ethyl, or represents cyclohexyl;

$R^6$ represents phenylalkyl or phenyl optionally having 1 or 2 carbon atoms in the alkyl part and which may each optionally be mono-, di- or trisubstituted in the phenyl part by substituents which are identical or different, or a five- or six-membered heteroaryl radical having from 1 to 3 heteroatoms which may be identical or different—in particular nitrogen, oxygen and/or sulphur—and which may optionally be mono- or disubstituted by substituents which may be identical or different, and/or be benzofused, possible phenyl and heteroaryl substituents in each case being:

fluorine, chlorine, bromine, cyano, nitro, amino, N-acetylamino, methyl, ethyl, n- or i-propyt, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoximinomethyl, methoximinoethyl, ethoximinomethyl, ethoximinoethyl or phenyl which may optionally be mono- to disubstituted by substituents which may be identical or different and comprise fluorine, chlorine, bromine, methyl, ethyl, methoxy, ethoxy, trifluoromethyl and/or trifluoromethoxy, and $R^7$ represents hydrogen or straight chain or branched alkyl having from 1 to 4 carbon atoms which may optionally be monosubstituted, possible substituents being: cyano, carboxyl, carbamoyl, or alkoxy, alkoxyalkoxy, alkylthio, alkylsulphinyl, alkylsulphonyl, alkoxycarbonyl, N-alkylaminocarbonyl, N,N-dialkylaminocarbonyl, trialkylsilyl or alkylsulphonylaminocarbonyl which may each be straight chain or branched and each have from 1 to 4 carbon atoms in the individual alkyl moieties, or heterocyclyl, where the heterocyclyl radical is a five- or six-membered, saturated or unsaturated heterocycle having from 1 to 3 heteroatoms which may be identical or different—in particular nitrogen, oxygen and/or sulphur—;

$R^7$ also represents haloqenoalkyl having 1 or 2 carbon atoms and from 1 to 5 halogen atoms which may be identical or different—in particular fluorine or chlorine—;

$R^7$ also represents alkenyl or alkinyl each having from 2 to 5 carbon atoms and which may each optionally be monosubstituted by halogen—in particular fluorine or chlorine;

$R^7$ also represents cyclopropyl which may optionally be mono- or disubstituted by substituents which may be identical or different and comprise fluorine, chlorine, methyl and/or ethyl, or represents cyclohexyl or $R^7$ represents phenylalkyl or phenyl optionally having 1 or 2 carbon atoms [lacuna] alkyl part and which may each optionally be mono- or disubstituted in the phenyl part by substituents which may be identical or different, possible phenyl substituents being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoximinomethyl, methoximinoethyl, ethoximinomethyl, ethoximinoethyl or phenyl which may optionally be mono- to disubstituted by substituents which may be identical or different and comprise fluorine, chlorine, bromine, methyl, ethyl, methoxy, ethoxy, trifluoromethyl and/or trifluoromethoxy.

In addition to the compounds given in the preparation examples, the following substituted triazolinones of the general formula (I) may be mentioned individually:

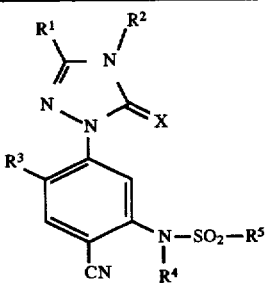

(I)

| R¹ | R² | R³ | R⁴ | R⁵ | X |
|---|---|---|---|---|---|
| H | H | F | H | $CH_3$ | O |
| Cl | H | Cl | H | $CH_3$ | O |
| Br | H | F | H | $CH_3$ | O |
| CN | H | Cl | H | $CH_3$ | O |
| $CH_3$ | H | F | H | $CH_3$ | O |
| $CF_3$ | H | Cl | H | $CH_3$ | O |
| $-CH=CH_2$ | H | F | H | $CH_3$ | O |
| $-CH_2-C\equiv CH$ | H | Cl | H | $CH_3$ | O |
| cyclohexyl | H | F | H | $CH_3$ | O |
| $-CH_2-C_6H_5$ | H | Cl | H | $CH_3$ | O |
| 4-Cl-$C_6H_4$- | H | F | H | $CH_3$ | O |
| $-O-CH_3$ | H | Cl | H | $CH_3$ | O |
| $-O-C_2H_5$ | H | F | H | $CH_3$ | O |
| $-O-$cyclopropyl | H | Cl | H | $CH_3$ | O |
| $-O-$(3-Cl-$C_6H_4$) | H | F | H | $CH_3$ | O |
| $-O-NH-CH_3$ | H | Cl | H | $CH_3$ | O |
| $-O-N(CH_3)_2$ | H | F | H | $CH_3$ | O |
| $-S-CH_3$ | H | Cl | H | $CH_3$ | O |
| $-S-C_2H_5$ | H | F | H | $CH_3$ | O |
| $-S-$(4-Cl-$C_6H_4$) | H | Cl | H | $CH_3$ | O |
| $-S(O)-CH_3$ | H | F | H | $CH_3$ | O |
| $-S(O)-C_2H_5$ | H | Cl | H | $CH_3$ | O |
| $-SO_2-CH_3$ | H | F | H | $CH_3$ | O |
| $-SO_2-C_2H_5$ | H | Cl | H | $CH_3$ | O |
| H | CN | F | H | $CH_3$ | O |
| Cl | CN | Cl | H | $CH_3$ | O |
| Br | CN | F | H | $CH_3$ | O |
| CN | CN | Cl | H | $CH_3$ | O |
| $CH_3$ | CN | F | H | $CH_3$ | O |
| $CF_3$ | CN | Cl | H | $CH_3$ | O |
| $-CH=CH_2$ | CN | F | H | $CH_3$ | O |
| $-CH_2-C\equiv CH$ | CN | Cl | H | $CH_3$ | O |

-continued

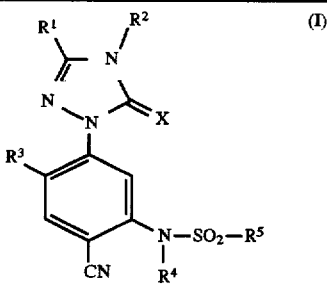

| R¹ | R² | R³ | R⁴ | R⁵ | X |
|---|---|---|---|---|---|
| cyclohexyl-H | CN | F | H | CH₃ | O |
| $-CH_2-C_6H_5$ | CN | Cl | H | CH₃ | O |
| 4-Cl-C₆H₄- | CN | F | H | CH₃ | O |
| $-O-CH_3$ | CN | Cl | H | CH₃ | O |
| $-O-C_2H_5$ | CN | F | H | CH₃ | O |
| $-O-\text{cyclopropyl}$ | CN | Cl | H | CH₃ | O |
| $-O-(3-Cl-C_6H_4)$ | CN | F | H | CH₃ | O |
| $-O-NH-CH_3$ | CN | Cl | H | CH₃ | O |
| $-O-N(CH_3)_2$ | CN | F | H | CH₃ | O |
| $-S-CH_3$ | CN | Cl | H | CH₃ | O |
| $-S-C_2H_5$ | CN | F | H | CH₃ | O |
| $-S-(4-Cl-C_6H_4)$ | CN | Cl | H | CH₃ | O |
| $-S(O)-CH_3$ | CN | F | H | CH₃ | O |
| $-S(O)-C_2H_5$ | CN | Cl | H | CH₃ | O |
| $-SO_2-CH_3$ | CN | F | H | CH₃ | O |
| $-SO_2-C_2H_5$ | CN | Cl | H | CH₃ | O |
| H | NH₂ | F | H | CH₃ | O |
| Cl | NH₂ | Cl | H | CH₃ | O |
| Br | NH₂ | F | H | CH₃ | O |
| CN | NH₂ | Cl | H | CH₃ | O |
| C₂H₅ | NH₂ | F | H | CH₃ | O |
| CClF₂ | NH₂ | Cl | H | CH₃ | O |
| $-CH=CH_2$ | NH₂ | F | H | CH₃ | O |
| $-CH_2-C\equiv CH$ | NH₂ | Cl | H | CH₃ | O |
| cyclohexyl-H | NH₂ | F | H | CH₃ | O |
| $-CH_2-C_6H_5$ | NH₂ | Cl | H | CH₃ | O |
| 4-Cl-C₆H₄- | NH₂ | F | H | CH₃ | O |
| $-O-CH_3$ | NH₂ | Cl | H | CH₃ | O |

-continued

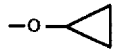

| R¹ | R² | R³ | R⁴ | R⁵ | X |
|---|---|---|---|---|---|
| —O—C₂H₅ | NH₂ | F | H | CH₃ | O |
| —O—cyclopropyl | NH₂ | Cl | H | CH₃ | O |
| —O—(3-chlorophenyl) | NH₂ | F | H | CH₃ | O |
| —O—NH—CH₃ | NH₂ | Cl | H | CH₃ | O |
| —O—N(CH₃)₂ | NH₂ | F | H | CH₃ | O |
| —S—CH₃ | NH₂ | Cl | H | CH₃ | O |
| —S—C₂H₅ | NH₂ | F | H | CH₃ | O |
| —S—(4-chlorophenyl) | NH₂ | Cl | H | CH₃ | O |
| —S(O)—CH₃ | NH₂ | F | H | CH₃ | O |
| —S(O)—C₂H₅ | NH₂ | Cl | H | CH₃ | O |
| —SO₂—CH₃ | NH₂ | F | H | CH₃ | O |
| —SO₂—C₂H₅ | NH₂ | Cl | H | CH₃ | O |
| H | CH | F | H | CH₃ | O |
| Cl | OH | Cl | H | CH₃ | O |
| Br | OH | F | H | CH₃ | O |
| CN | OH | Cl | H | CH₃ | O |
| CH₃ | OH | F | H | CH₃ | O |
| CF₃ | OH | Cl | H | CH₃ | O |
| —CH=CH₂ | OH | F | H | CH₃ | O |
| —CH₂—C≡CH | OH | Cl | H | CH₃ | O |
| cyclohexyl | OH | F | H | CH₃ | O |
| —CH₂—C₆H₅ | OH | Cl | H | CH₃ | O |
| 4-chlorophenyl | OH | F | H | CH₃ | O |
| —O—CH₃ | OH | Cl | H | CH₃ | O |
| —O—C₂H₅ | OH | F | H | CH₃ | O |
| —O—cyclopropyl | OH | Cl | H | CH₃ | O |
| —O—(3-chlorophenyl) | OH | F | H | CH₃ | O |
| —O—NH—CH₃ | OH | Cl | H | CH₃ | O |
| —O—N(CH₃)₂ | OH | F | H | CH₃ | O |

-continued

| R¹ | R² | R³ | R⁴ | R⁵ | X |
|---|---|---|---|---|---|
| —S—CH₃ | OH | Cl | H | CH₃ | O |
| —S—C₂H₅ | OH | F | H | CH₃ | O |
|  | OH | Cl | H | CH₃ | O |
| —S(O)—CH₃ | OH | F | H | CH₃ | O |
| —S(O)—C₂H₅ | OH | Cl | H | CH₃ | O |
| —SO₂—CH₃ | OH | F | H | CH₃ | O |
| —SO₂—C₂H₅ | OH | Cl | H | CH₃ | O |
| H | C₂H₅ | F | H | CH₃ | O |
| Cl | C₂H₅ | Cl | H | CH₃ | O |
| Br | C₂H₅ | F | H | CH₃ | O |
| CN | C₂H₅ | Cl | H | CH₃ | O |
| CH₃ | C₂H₅ | F | H | CH₃ | O |
| CClF₂ | C₂H₅ | Cl | H | CH₃ | O |
| —CH=CH₂ | C₂H₅ | F | H | CH₃ | O |
| —CH₂—C≡CH | C₂H₅ | Cl | H | CH₃ | O |
|  | C₂H₅ | F | H | CH₃ | O |
| —CH₂—C₆H₅ | C₂H₅ | Cl | H | CH₃ | O |
| 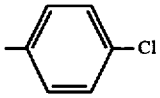 | C₂H₅ | F | H | CH₃ | O |
| —O—CH₃ | C₂H₅ | Cl | H | CH₃ | O |
| —O—C₂H₅ | C₂H₅ | F | H | CH₃ | O |
|  | C₂H₅ | Cl | H | CH₃ | O |
| 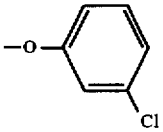 | C₂H₅ | F | H | CH₃ | O |
| —O—NH—CH₃ | C₂H₅ | Cl | H | CH₃ | O |
| —O—N(CH₃)₂ | C₂H₅ | F | H | CH₃ | O |
| —S—CH₃ | C₂H₅ | Cl | H | CH₃ | O |
| —S—C₂H₅ | C₂H₅ | F | H | CH₃ | O |
| 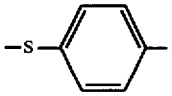 | C₂H₅ | Cl | H | CH₃ | O |
| —S(O)—CH₃ | C₂H₅ | F | H | CH₃ | O |
| —S(O)—C₂H₅ | C₂H₅ | Cl | H | CH₃ | O |
| —SO₂—CH₃ | C₂H₅ | F | H | CH₃ | O |
| —SO₂—C₂H₅ | C₂H₅ | Cl | H | CH₃ | O |
| H | —O—C₂H₅ | F | H | CH₃ | O |
| Cl | —O—C₂H₅ | Cl | H | CH₃ | O |

-continued

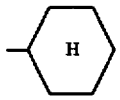

(I)

| R¹ | R² | R³ | R⁴ | R⁵ | X |
|---|---|---|---|---|---|
| Br | —O—C₂H₅ | F | H | CH₃ | O |
| CN | —O—C₂H₅ | Cl | H | CH₃ | O |
| CH₃ | —O—C₂H₅ | F | H | CH₃ | O |
| CF₃ | —O—C₂H₅ | Cl | H | CH₃ | O |
| —CH=CH₂ | —O—C₂H₅ | F | H | CH₃ | O |
| —CH₂—C≡CH | —O—C₂H₅ | Cl | H | CH₃ | O |
|  | —O—C₂H₅ | F | H | CH₃ | O |
| —CH₂—C₆H₅ | —O—C₂H₅ | Cl | H | CH₃ | O |
| 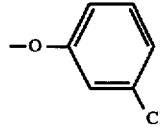 | —O—C₂H₅ | F | H | CH₃ | O |
| —O—CH₃ | —O—C₂H₅ | Cl | H | CH₃ | O |
| —O—C₂H₅ | —O—CHF₂ | F | H | CH₃ | O |
| 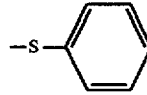 | —O—CHF₂ | Cl | H | CH₃ | O |
| 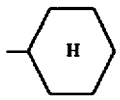 | —O—CHF₂ | F | H | CH₃ | O |
| —O—N—CH₃ | —O—CHF₂ | Cl | H | CH₃ | O |
| —O—N(CH₃)₂ | —O—CHF₂ | F | H | CH₃ | O |
| —S—CH₃ | —O—CHF₂ | Cl | H | CH₃ | O |
| —S—C₂H₅ | —O—CHF₂ | F | H | CH₃ | O |
| —S—C₆H₄—Cl | —O—CHF₂ | Cl | H | CH₃ | O |
| —S(O)—CH₃ | —O—CHF₂ | F | H | CH₃ | O |
| —S(O)—C₂H₅ | —O—CHF₂ | Cl | H | CH₃ | O |
| —SO₂—CH₃ | —O—CHF₂ | F | H | CH₃ | O |
| —SO₂—C₂H₅ | —O—CHF₂ | Cl | H | CH₃ | O |
| H | —N=C(CH₃)₂ | F | H | CH₃ | O |
| Cl | —N=C(CH₃)₂ | Cl | H | CH₃ | O |
| Br | —N=C(CH₃)₂ | F | H | CH₃ | O |
| CN | —N=C(CH₃)₂ | Cl | H | CH₃ | O |
| CH₃ | —N=C(CH₃)₂ | F | H | CH₃ | O |
| CF₃ | —N=C(CH₃)₂ | Cl | H | CH₃ | O |
| —CH=CH₂ | —N=C(CH₃)₂ | F | H | CH₃ | O |
| —CH₂—C≡CH | —N=C(CH₃)₂ | Cl | H | CH₃ | O |
|  | —N=C(CH₃)₂ | F | H | CH₃ | O |
| —CH₂—C₆H₅ | —N=C(CH₃)₂ | Cl | H | CH₃ | O |

-continued

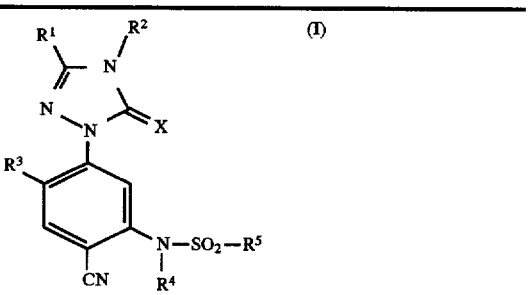

| R¹ | R² | R³ | R⁴ | R⁵ | X |
|---|---|---|---|---|---|
| 4-Cl-C₆H₄- | -N=C(CH₃)₂ | F | H | CH₃ | O |
| -O-CH₃ | -N=CH-C₆H₅ | Cl | H | CH₃ | O |
| -O-C₂H₅ | -N=CH-C₆H₅ | F | H | CH₃ | O |
| -O-cyclopropyl | -N=CH-C₆H₅ | Cl | H | CH₃ | O |
| -O-(3-Cl-C₆H₄) | -N=CH-C₆H₅ | F | H | CH₃ | O |
| -O-NH-CH₃ | -N=CH-C₆H₅ | Cl | H | CH₃ | O |
| -O-N(CH₃)₂ | -N=CH-C₆H₅ | F | H | CH₃ | O |
| -S-CH₃ | -N=CH-C₆H₅ | Cl | H | CH₃ | O |
| -S-C₂H₅ | -N=CH-C₆H₅ | F | H | CH₃ | O |
| -S-(4-Cl-C₆H₄) | -N=CH-C₆H₅ | Cl | H | CH₃ | O |
| -S(O)-CH₃ | -N=CH-C₆H₅ | F | H | CH₃ | O |
| -S(O)-C₂H₅ | -N=CH-C₆H₅ | Cl | H | CH₃ | O |
| -SO₂-CH₃ | -N=CH-C₆H₅ | F | H | CH₃ | O |
| -SO₂-C₂H₅ | -N=CH-C₆H₅ | Cl | H | CH₃ | O |
| CF₃ | CH₃ | Cl | H | CH₃ | O |
| -CHF₂ | CH₃ | Cl | H | CH₃ | O |
| CH₃ | -O-CH₃ | H | H | CH₃ | O |
| CH₃ | -O-C₂H₅ | F | H | CH₃ | O |
| CH₃ | NH₂ | F | H | CH₃ | O |
| CF₃ | NH₂ | Cl | H | CH₃ | O |
| CH₃ | -CHF₂ | F | H | CH₃ | O |
| CF₃ | -CHF₂ | Cl | H | CH₃ | O |
| CF₃ | C₂H₅ | H | H | CH₃ | O |
| CF₃ | CH₃ | F | H | C₂H₅ | O |
| -CHF₂ | CH₃ | Cl | H | C₂H₅ | O |
| CH₃ | -O-CH₃ | F | H | C₂H₅ | O |
| CH₃ | -O-C₂H₅ | Cl | H | C₂H₅ | O |
| CH₃ | NH₂ | F | H | C₂H₅ | O |
| CF₃ | NH₂ | Cl | H | C₂H₅ | O |
| CH₃ | -CHF₂ | F | H | C₂H₅ | O |
| CF₃ | -CHF₂ | Cl | H | C₂H₅ | O |
| CF₃ | C₂H₅ | Cl | H | C₂H₅ | O |
| CF₃ | CH₃ | F | H | n-C₃H₇ | O |
| -CHF₂ | CH₃ | Cl | H | n-C₃H₇ | O |
| CH₃ | -O-CH₃ | F | H | n-C₃H₇ | O |
| CH₃ | -O-C₂H₅ | Cl | H | n-C₃H₇ | O |
| CH₃ | NH₂ | F | H | n-C₃H₇ | O |
| CF₃ | NH₂ | Cl | H | n-C₃H₇ | O |
| CH₃ | -CHF₂ | F | H | n-C₃H₇ | O |
| CF₃ | -CHF₂ | Cl | H | n-C₃H₇ | O |
| CF₃ | C₂H₅ | Cl | H | n-C₃H₇ | O |
| CF₃ | CH₃ | F | H | i-C₃H₇ | O |
| -CHF₂ | CH₃ | Cl | H | i-C₃H₇ | O |
| CH₃ | -O-CH₃ | F | H | i-C₃H₇ | O |

-continued

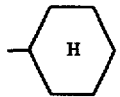

| R¹ | R² | R³ | R⁴ | R⁵ | X |
|---|---|---|---|---|---|
| CH₃ | —O—C₂H₅ | Cl | H | i-C₃H₇ | O |
| CH₃ | NH₂ | F | H | i-C₃H₇ | O |
| CF₃ | NH₂ | Cl | H | i-C₃H₇ | O |
| CH₃ | —CHF₂ | F | H | i-C₃H₇ | O |
| CF₃ | —CHF₂ | Cl | H | i-C₃H₇ | O |
| CF₃ | C₂H₅ | Cl | H | i-C₃H₇ | O |
| CF₃ | CH₃ | F | H | n-C₄H₉ | O |
| —CHF₂ | CH₃ | Cl | H | n-C₄H₉ | O |
| CH₃ | —O—CH₃ | F | H | n-C₄H₉ | O |
| CH₃ | —O—C₂H₅ | Cl | H | n-C₄H₉ | O |
| CH₃ | NH₂ | Cl | H | n-C₄H₉ | O |
| CF₃ | NH₂ | F | H | n-C₄H₉ | O |
| CH₃ | —CHF₂ | Cl | H | n-C₄H₉ | O |
| CF₃ | —CHF₂ | F | H | n-C₄H₉ | O |
| CF₃ | C₂H₅ | Cl | H | n-C₄H₉ | O |
| CF₃ | CH₃ | F | H | s-C₄H₉ | O |
| —CHF₂ | CH₃ | Cl | H | s-C₄H₉ | O |
| CH₃ | —O—CH₃ | F | H | s-C₄H₉ | O |
| CH₃ | —O—C₂H₅ | Cl | H | s-C₄H₉ | O |
| CH₃ | NH₂ | F | H | s-C₄H₉ | O |
| CF₃ | NH₂ | Cl | H | s-C₄H₉ | O |
| CH₃ | —CHF₂ | F | H | s-C₄H₉ | O |
| CF₃ | —CHF₂ | Cl | H | s-C₄H₉ | O |
| CF₃ | C₂H₅ | Cl | H | s-C₄H₉ | O |
| CF₃ | CH₃ | F | H | CF₃ | O |
| —CHF₂ | CH₃ | Cl | H | CF₃ | O |
| CH₃ | —O—CH₃ | F | H | CF₃ | O |
| CH₃ | —O—C₂H₅ | Cl | H | CF₃ | O |
| CH₃ | NH₂ | F | H | CF₃ | O |
| CF₃ | NH₂ | Cl | H | CF₃ | O |
| CH₃ | —CHF₂ | F | H | CF₃ | O |
| CF₃ | —CHF₂ | Cl | H | CF₃ | O |
| CF₃ | C₂H₅ | Cl | H | CF₃ | O |
| CF₃ | CH₃ | F | H | 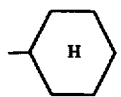 | O |
| —CHF₂ | CH₃ | Cl | H | 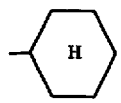 | O |
| CH₃ | —O—CH₃ | F | H | 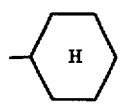 | O |
| CH₃ | —O—C₂H₅ | Cl | H | 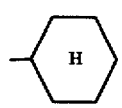 | O |
| CH₃ | NH₂ | F | H | 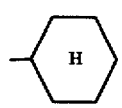 | O |

-continued

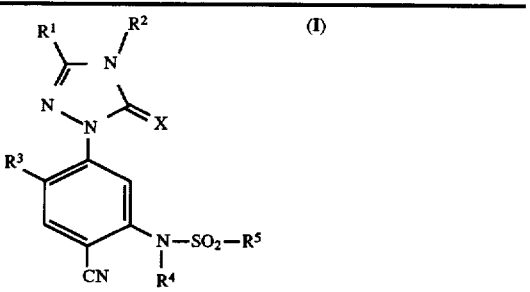

| R¹ | R² | R³ | R⁴ | R⁵ | X |
|---|---|---|---|---|---|
| CF₃ | NH₂ | Cl | H | cyclohexyl-H | O |
| CH₃ | —CHF₂ | F | H | cyclohexyl-H | O |
| CF₃ | —CHF₂ | Cl | H | cyclohexyl-H | O |
| CF₃ | C₂H₅ | Cl | H | cyclohexyl-H | O |
| CF₃ | CH₃ | F | H | C₆H₅ | O |
| —CHF₂ | CH₃ | Cl | H | C₆H₅ | O |
| CH₃ | —O—CH₃ | Cl | H | C₆H₅ | O |
| CH₃ | —O—C₂H₅ | F | H | C₆H₅ | O |
| CH₃ | NH₂ | Cl | H | C₆H₅ | O |
| CF₃ | NH₂ | F | H | C₆H₅ | O |
| CH₃ | —CHF₂ | Cl | H | C₆H₅ | O |
| CF₃ | —CHF₂ | F | H | C₆H₅ | O |
| CF₃ | C₂H₅ | Cl | H | C₆H₅ | O |
| CF₃ | CH₃ | F | H | 4-CH₃-C₆H₄ | O |
| —CHF₂ | CH₃ | Cl | H | 4-CH₃-C₆H₄ | O |
| CH₃ | —O—CH₃ | F | H | 4-CH₃-C₆H₄ | O |
| CH₃ | —O—C₂H₅ | Cl | H | 4-CH₃-C₆H₄ | O |
| CH₃ | NH₂ | F | H | 4-CH₃-C₆H₄ | O |
| CF₃ | NH₂ | Cl | H | 4-CH₃-C₆H₄ | O |

-continued

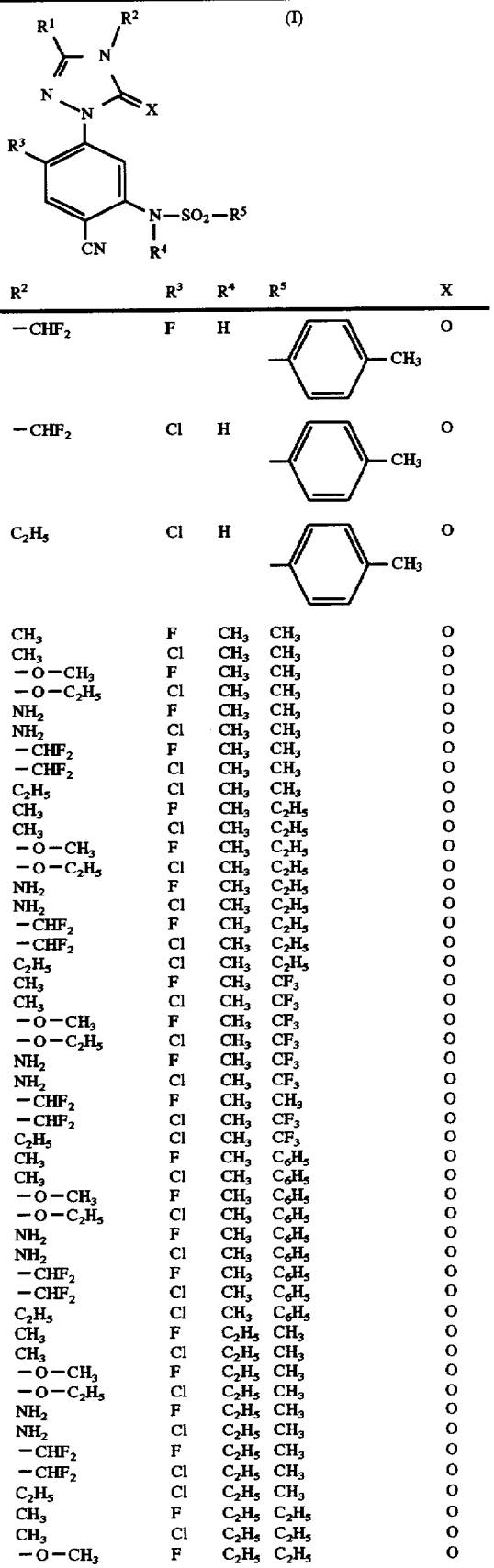

| R¹ | R² | R³ | R⁴ | R⁵ | X |
|---|---|---|---|---|---|
| CH₃ | —CHF₂ | F | H | ![p-tolyl]—CH₃ | O |
| CF₃ | —CHF₂ | Cl | H | ![p-tolyl]—CH₃ | O |
| CF₃ | C₂H₅ | Cl | H | ![p-tolyl]—CH₃ | O |
| CF₃ | CH₃ | F | CH₃ | CH₃ | O |
| —CHF₂ | CH₃ | Cl | CH₃ | CH₃ | O |
| CH₃ | —O—CH₃ | F | CH₃ | CH₃ | O |
| CH₃ | —O—C₂H₅ | Cl | CH₃ | CH₃ | O |
| CH₃ | NH₂ | F | CH₃ | CH₃ | O |
| CF₃ | NH₂ | Cl | CH₃ | CH₃ | O |
| CH₃ | —CHF₂ | F | CH₃ | CH₃ | O |
| CF₃ | —CHF₂ | Cl | CH₃ | CH₃ | O |
| CF₃ | C₂H₅ | Cl | CH₃ | CH₃ | O |
| CF₃ | CH₃ | F | CH₃ | C₂H₅ | O |
| —CHF₂ | CH₃ | Cl | CH₃ | C₂H₅ | O |
| CH₃ | —O—CH₃ | F | CH₃ | C₂H₅ | O |
| CH₃ | —O—C₂H₅ | Cl | CH₃ | C₂H₅ | O |
| CH₃ | NH₂ | F | CH₃ | C₂H₅ | O |
| CF₃ | NH₂ | Cl | CH₃ | C₂H₅ | O |
| CH₃ | —CHF₂ | F | CH₃ | C₂H₅ | O |
| CF₃ | —CHF₂ | Cl | CH₃ | C₂H₅ | O |
| CF₃ | C₂H₅ | Cl | CH₃ | C₂H₅ | O |
| CF₃ | CH₃ | F | CH₃ | CF₃ | O |
| —CHF₂ | CH₃ | Cl | CH₃ | CF₃ | O |
| CH₃ | —O—CH₃ | F | CH₃ | CF₃ | O |
| CH₃ | —O—C₂H₅ | Cl | CH₃ | CF₃ | O |
| CH₃ | NH₂ | F | CH₃ | CF₃ | O |
| CF₃ | NH₂ | Cl | CH₃ | CF₃ | O |
| CH₃ | —CHF₂ | F | CH₃ | CH₃ | O |
| CF₃ | —CHF₂ | Cl | CH₃ | CF₃ | O |
| CF₃ | C₂H₅ | Cl | CH₃ | CF₃ | O |
| CF₃ | CH₃ | F | CH₃ | C₆H₅ | O |
| —CHF₂ | CH₃ | Cl | CH₃ | C₆H₅ | O |
| CH₃ | —O—CH₃ | F | CH₃ | C₆H₅ | O |
| CH₃ | —O—C₂H₅ | Cl | CH₃ | C₆H₅ | O |
| CH₃ | NH₂ | F | CH₃ | C₆H₅ | O |
| CF₃ | NH₂ | Cl | CH₃ | C₆H₅ | O |
| CH₃ | —CHF₂ | F | CH₃ | C₆H₅ | O |
| CF₃ | —CHF₂ | Cl | CH₃ | C₆H₅ | O |
| CF₃ | C₂H₅ | Cl | CH₃ | C₆H₅ | O |
| CF₃ | CH₃ | F | C₂H₅ | CH₃ | O |
| —CHF₂ | CH₃ | Cl | C₂H₅ | CH₃ | O |
| CH₃ | —O—CH₃ | F | C₂H₅ | CH₃ | O |
| CH₃ | —O—C₂H₅ | Cl | C₂H₅ | CH₃ | O |
| CH₃ | NH₂ | F | C₂H₅ | CH₃ | O |
| CF₃ | NH₂ | Cl | C₂H₅ | CH₃ | O |
| CH₃ | —CHF₂ | F | C₂H₅ | CH₃ | O |
| CF₃ | —CHF₂ | Cl | C₂H₅ | CH₃ | O |
| CF₃ | C₂H₅ | Cl | C₂H₅ | CH₃ | O |
| CF₃ | CH₃ | F | C₂H₅ | C₂H₅ | O |
| —CHF₂ | CH₃ | Cl | C₂H₅ | C₂H₅ | O |
| CH₃ | —O—CH₃ | F | C₂H₅ | C₂H₅ | O |

-continued

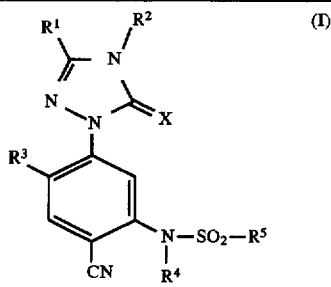

| R¹ | R² | R³ | R⁴ | R⁵ | X |
|---|---|---|---|---|---|
| CH₃ | —O—C₂H₅ | Cl | C₂H₅ | C₂H₅ | O |
| CH₃ | NH₂ | F | C₂H₅ | C₂H₅ | O |
| CF₃ | NH₂ | Cl | C₂H₅ | C₂H₅ | O |
| CH₃ | —CHF₂ | F | C₂H₅ | C₂H₅ | O |
| CF₃ | —CHF₂ | Cl | C₂H₅ | C₂H₅ | O |
| CF₃ | C₂H₅ | Cl | C₂H₅ | C₂H₅ | O |
| CF₃ | CH₃ | F | C₂H₅ | CF₃ | O |
| —CHF₂ | CH₃ | Cl | C₂H₅ | CF₃ | O |
| CH₃ | —O—CH₃ | F | C₂H₅ | CF₃ | O |
| CH₃ | —O—C₂H₅ | Cl | C₂H₅ | CF₃ | O |
| CH₃ | NH₂ | F | C₂H₅ | CF₃ | O |
| CF₃ | NH₂ | Cl | C₂H₅ | CF₃ | O |
| CH₃ | —CHF₂ | F | C₂H₅ | CF₃ | O |
| CF₃ | —CHF₂ | Cl | C₂H₅ | CF₃ | O |
| CF₃ | C₂H₅ | Cl | C₂H₅ | CF₃ | O |
| CF₃ | CH₃ | F | C₂H₅ | C₆H₅ | O |
| —CHF₂ | CH₃ | Cl | C₂H₅ | C₆H₅ | O |
| CH₃ | —O—CH₃ | F | C₂H₅ | C₆H₅ | O |
| CH₃ | —O—C₂H₅ | Cl | C₂H₅ | C₆H₅ | O |
| CH₃ | NH₂ | F | C₂H₅ | C₆H₅ | O |
| CF₃ | NH₂ | Cl | C₂H₅ | C₆H₅ | O |
| CH₃ | —CHF₂ | F | C₂H₅ | C₆H₅ | O |
| CF₃ | —CHF₂ | Cl | C₂H₅ | C₆H₅ | O |
| CF₃ | C₂H₅ | Cl | C₂H₅ | C₆H₅ | O |
| CF₃ | CH₃ | Br | H | CH₃ | O |
| —CHF₂ | CH₃ | Br | H | CH₃ | O |
| CH₃ | —O—CH₃ | Br | H | CH₃ | O |
| CH₃ | —O—C₂H₅ | Br | H | CH₃ | O |
| CH₃ | NH₂ | Br | H | CH₃ | O |
| —CF₃ | NH₂ | Br | H | CH₃ | O |
| CH₃ | —CHF₂ | Br | H | CH₃ | O |
| CF₃ | —CHF₂ | Br | H | CH₃ | O |
| CF₃ | C₂H₅ | Br | H | CH₃ | O |
| CF₃ | CH₃ | CH₃ | H | CH₃ | O |
| —CHF₂ | CH₃ | CH₃ | H | CH₃ | O |
| CH₃ | —O—CH₃ | CH₃ | H | CH₃ | O |
| CH₃ | —O—C₂H₅ | CH₃ | H | CH₃ | O |
| CH₃ | NH₂ | CH₃ | H | CH₃ | O |
| CF₃ | NH₂ | CH₃ | H | CH₃ | O |
| CH₃ | —CHF₂ | CH₃ | H | CH₃ | O |
| CF₃ | —CHF₂ | CH₃ | H | CH₃ | O |
| CF₃ | C₂H₅ | CH₃ | H | CH₃ | O |
| CF₃ | CH₃ | F | H | CH₃ | S |
| —CHF₂ | CH₃ | Cl | H | CH₃ | S |
| CH₃ | —O—CH₃ | F | H | CH₃ | S |
| CH₃ | —O—C₂H₅ | Cl | H | CH₃ | S |
| CH₃ | NH₂ | F | H | CH₃ | S |
| CF₃ | NH₂ | Cl | H | CH₃ | S |
| CH₃ | —CHF₂ | F | H | CH₃ | S |
| CF₃ | —CHF₂ | Cl | H | CH₃ | S |
| CF₃ | C₂H₅ | Cl | H | CH₃ | S |
| CF₃ | CH₃ | F | H | C₂H₅ | S |
| —CHF₂ | CH₃ | Cl | H | C₂H₅ | S |
| CH₃ | —O—CH₃ | F | H | C₂H₅ | S |
| CH₃ | —O—C₂H₅ | Cl | H | C₂H₅ | S |
| CH₃ | NH₂ | F | H | C₂H₅ | S |
| CF₃ | NH₂ | Cl | H | C₂H₅ | S |
| CH₃ | —CHF₂ | F | H | C₂H₅ | S |
| CF₃ | —CHF₂ | Cl | H | C₂H₅ | S |
| CF₃ | C₂H₅ | Cl | H | C₂H₅ | S |

If, for example, 4-methyl-3-trifluoromethyl-1,2,4-triazolin-5-one and 2-methylsulphonamido-4,5-difluorobenzonitrile are used as starting materials, the reaction sequence of process (a) of the invention can be represented by the following formula scheme:

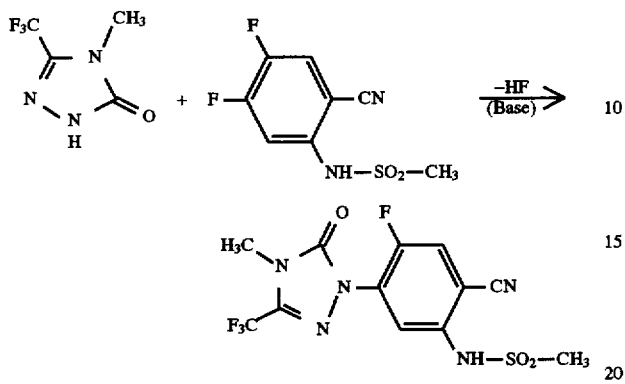

If, for example, 1-(4-cyano-2,5-difluorophenyl)-4-methyl-3-trifluoromethyl-1,2,4-triazolin-5-one and N-methyl-methanesulphonamide are used as starting materials, the reaction sequence of process (b) can be represented by the following formula scheme:

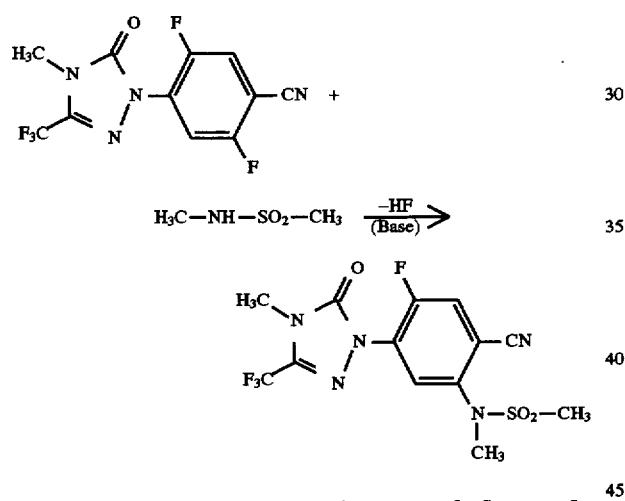

If, for example, 1-(4-cyano-2-fluoro-5-methanesulphonamido-phenyl)-4-amino-3-trifluoromethyl-1,2,4-triazolin-5-one and sodium nitrite are used as starting materials, the reaction sequence of process (c) of the invention can be represented by the following formula scheme:

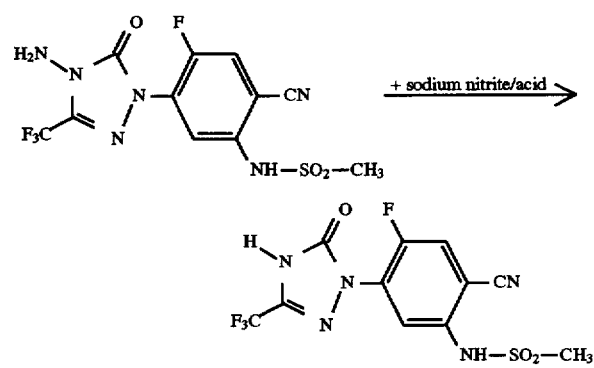

If, for example, 1-[4-cyano-2-fluoro-5-(N-methyl-methanesulphonamido)-phenyl]-3-trifluoromethyl-(4H)-1,2,4-triazolin-5-one and chlorodifluoromethane are used as starting materials, the reaction sequence of process (d) of the invention can be represented by the following formula scheme:

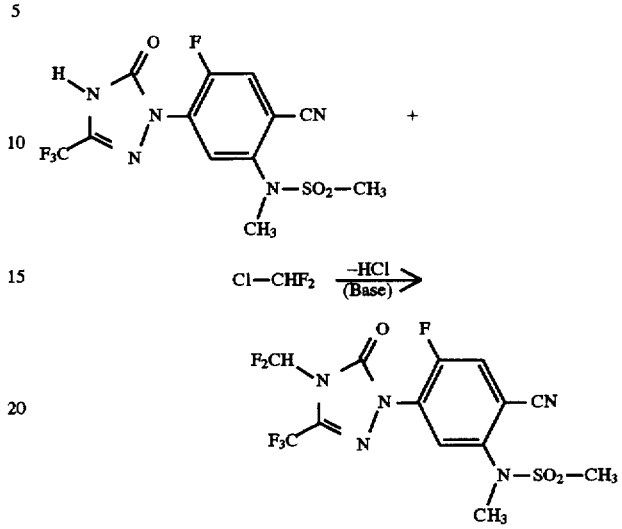

If, for example, 1-[4-cyano-2-fluoro-5-methanesulphonamido-phenyl]-4-methyl-3-trifluoromethyl-1,2,4-triazolin-5-one and iodomethane are used as starting materials, the reaction sequence of process (e) of the invention can be represented by the following formula scheme:

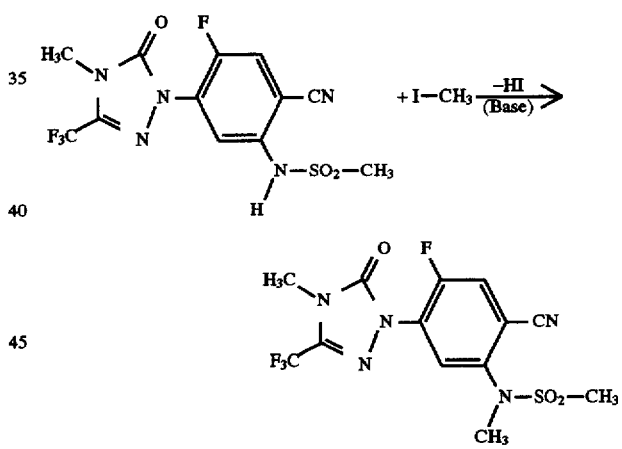

If, for example, 1-(4-cyano-2-fluoro-5-methylaminophenyl)-4-methyl-3-trifluoromethyl-1,2,4-triazolin-5-one and methanesulphonyl chloride are used as starting materials, the reaction sequence of process (f) of the invention can be represented by the following formula scheme:

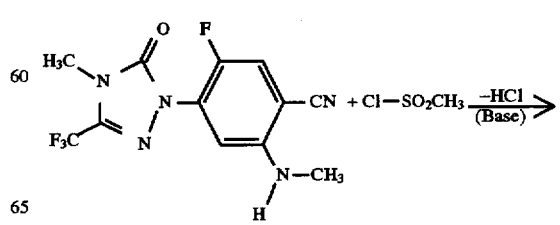

-continued

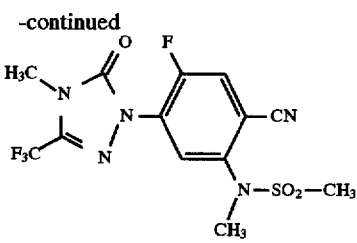

The 1H-triazolinones required as starting materials for carrying out process (a) of the invention are generally defined by the formula (II). In this formula (II), $R^1$, $R^2$ and X preferably and particularly preferably represent those radicals which have already been mentioned as preferred and particularly preferred for these substituents in connection with the description of the compounds of the invention of the formula (I).

The 1H-triazolinones of the formula (II) are known or obtainable by analogy with known processes (cf., for example, EP 399 294; U.S. Pat. No. 4,477,459; DE 27 16 707; U.S. Pat. No. 3,780,052; J. Med. Chem. 14, 335–338 [1971]; DE 20 29 375). The compound 4-amino-3-trifluoromethyl-1H-1,2,4-triazolin-5-one is not yet known. It is obtained by reacting hydrazine hydrate first with diphenyl carbonate and subsequently with trifluoroacetic acid at temperatures between –20° C. and +200° C. (cf. also the preparation examples).

The halogenobenzene derivatives further required as starting materials for carrying out process (a) of the invention are generally defined by the formula (III). In this formula (III), $R^3$, $R^4$ and $R^5$ preferably and particularly preferably represent those radicals which have already been mentioned as preferred and particularly preferred for these substituents in connection with the description. of the compounds of the invention of the formula (I). $Hal^1$ preferably represents fluorine, chlorine or bromine, particularly fluorine or chlorine.

The halogenobenzene derivatives of the formula (III) are not yet known and the likewise form part of the subject matter of the invention. They are obtained when 2-halogenobenzonitriles of the formula (X),

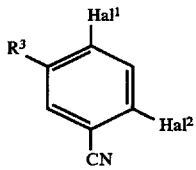

(X)

in which
$Hal^1$ and $R^3$ are as defined above and
$Hal^2$ represents halogen,
are reacted with sulphonamides of the formula (V),

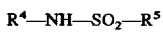 (V)

in which
$R^4$ and $R^5$ are as defined above, analogously to process (b) of the invention, optionally in the presence of a diluent such as, for example, acetonitrile and optionally in the presence of a reaction aid such as, for example, potassium carbonate at temperatures between –20° C. and +120° C.

2-Halogenobenzonitriles of the formula (X) are known or obtainable by analogy with known processes (cf., for example, EP 191 181; EP 441 004; EP 431 373). The compound 5-chloro-2,4-difluorobenzonitrile is not yet known. It is obtained by reacting the known compound 2,4,5-trichlorobenzonitrile (cf., for example, EP 441 004) with potassium fluoride optionally in the presence of a diluent such as, for example, tetramethylene sulphone at temperatures between 100° C. and 200° C. (cf. also the preparation examples).

The substituted triazolinones required as starting materials for carrying out process (b) of the invention are generally defined by the formula (IV). In this formula (IV), $R^1$, $R^2$, $R^3$ and X preferably and particularly preferably represent those radicals which have already been mentioned as preferred and particularly preferred for these substituents in connection with the description of the substances of the invention of the formula (I). $Hal^2$ preferably represents fluorine, chlorine or bromine, in particular fluorine or chlorine.

The substituted triazolinones of the formula (IV) are not yet known. They are nevertheless the subject of our own unpublished patent applications and obtainable by means of the processes described therein, for example, when 1H-triazolinones of the formula (II),

 (II)

in which
$R^1$, $R^2$ and X are as defined above,
are reacted with 2-halogenobenzonitriles of the formula (X),

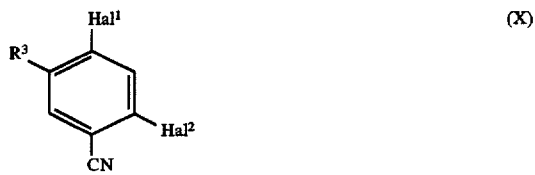 (X)

in which
$Hal^1$ and $R^3$ are as defined above and
$Hal^2$ represents halogen, analogously to process (a) of the invention optionally in the presence of a diluent such as, for example, acetonitrile and optionally in the presence of a reaction aid such as, for example, potassium carbonate at temperatures between –20° C. and 120° C.

The sulphonamides further required as starting materials for carrying out process (b) of the invention are generally defined by the formula (V). In this formula (V), $R^4$ and $R^5$ preferably represent those radicals which have alreadybeen mentioned as preferred and particularly preferred for these substituents in connection with the description of the substances of the invention of the formula (I).

The sulphonamides of the formula (V) are compounds generally known in organic chemistry.

The substituted triazolinones required as starting materials for carrying out process (c) of the invention are generally defined by the formula (Ia). In this formula (Ia), $R^1$, $R^3$, $R^4$, $R^5$ and X preferably and particularly preferably represent those radicals which have already been mentioned as preferred and particularly preferred for these substituents in connection with the description of the substances of the invention of the formula (I). $R^{2-1}$ preferably represents amino.

The substituted triazolinones of the formula (Ia) are compounds of the invention and obtainable by means of processes (a), (b), (e) and/or (f) of the invention.

The substituted triazolinones required as starting materials for carrying out process (d) of the invention are generally defined by the formula (Ib). In this formula (Ib), $R^1$, $R^3$, $R^4$, $R^5$ and X preferably and particularly preferably represent those radicals which have alreadybeen mentioned as preferred and particularly preferred for these substitutents in connection with the description of the substances of the invention of the formula (I). $R^{2-2}$ preferably represents hydrogen.

The substituted triazolinones of the formula (Ib) are compounds of the invention and obtainable by means of processes (a), (b), (c), (e) and/or (f) of the invention.

The alkylating agents further required as starting materials for carrying out process (d) of the invention are generally defined by the formula (VI). In this formula (VI), $R^{2-3}$ preferably and particularly preferably represents those radicals which have already been mentioned as preferred and particularly preferred for the substituents $R^6$ in connection with the description of the substances of the invention of the formula (I), with the exception of the optionally substituted aryl radicals. $E^1$ preferably represents a leaving group customary in alkylating agents, such as, for example, halogen, in particular chlorine, bromine or iodine, or represents alkylsulphonyloxy, alkoxysulphonyloxy or arylsulphonyloxy, such as, in particular, methanesulphonyloxy, trifluoromethanesulphonyloxy, methoxysulphonyloxy, ethoxysulphonyloxy or p-toluenesulphonyloxy, which may each optionally be substituted.

The alkylating agents of the formula (VI) are compounds generally known in organic chemistry.

The substituted triazolinones required as starting materials for carrying out process (e) of the invention are generally defined by the formula (Ic). In this formula (Ic), $R^1$, $R^2$, $R^3$, $R^5$ and X preferably and particularly preferably represent those radicals which have already been mentioned as preferred and particularly preferred for these substitutents in connection with the description of the substances of the invention of the formula (I). The substituted triazolinones of the formula (Ic) are compounds of the invention and obtainable by means of processes (a), (b), (c), (d) and/or (f) of the invention.

The alkylating agents further required as starting materials for carrying out process (e) of the invention are generally defined by the formula (VII). In this formula (VII), $R^{4-1}$ preferably and particularly preferably represents those radicals which have already been mentioned as preferred and particularly preferred for the substituents $R^6$ in connection with the description of the substances of the invention of the formula (I), with the exception of the optionally substituted aryl radicals. $E^2$ preferably represents a leaving group customary in alkylating agents, such as, for example, halogen, in particular chlorine, bromine or iodine, or represents alkylsulphonyloxy, alkoxysulphonyloxy or arylsulphonyloxy, such as, in particular, methanesulphonyloxy, trifluoromethanesulphonyloxy, methoxysulphonyloxy, ethoxysulphonyloxy or p-toluenesulphonyloxy, which may each optionally be substituted.

The alkylating agents of the formula (VII) are compounds generally known in organic chemistry.

The substituted triazolinones required as starting materials for carrying out process (f) of the invention are generally defined by the formula (VIII). In this formula (VIII), $R^1$, $R^2$, $R^3$, $R^4$ and X preferably and particularly preferably represent those radicals which have alreadybeen mentioned as preferred and particularly preferred for these substitutents in connection with the description of the substances of the invention of the formula (I).

The substituted triazolinones of the formula (VIII) are not yet known. However, they are the subject of the Applicant's as yet unpublished patent applications and obtainable by means of the processes described therein, for example by reacting substituted triazolinones of the formula (IV),

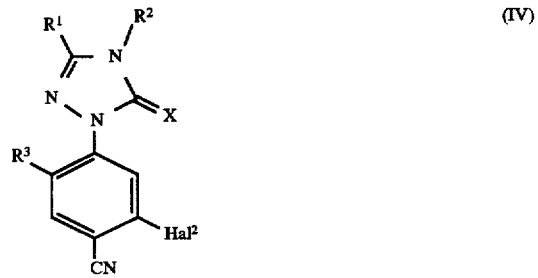

in which $R^1$, $R^2$, $R^3$ and X are as defined above and $Hal^2$ represents halogen, with amines of the formula (XI),

$$R^4-NH_2 \qquad (XI)$$

in which $R^4$ is as defined above, optionally in the presence of a diluent such as, for example, acetonitrile and optionally in the presence of a reaction aid such as, for example, potassium carbonate at temperatures between −20° C. and +120° C.

Amines of the formula (XI) are compounds generally known in organic chemistry.

The sulphonyl halides further required as starting materials for carrying out process (f) of the invention are generally defined by the formula (IX). In this formula (IX), $R^5$ preferably and particularly preferably represents those radicals which have already been mentioned as preferred and particularly preferred for these substituents in connection with the description of the substances of the formula (I) of the invention. $Hal^3$ preferably represents fluorine, chlorine or bromine, in particular chlorine or bromine.

The sulphonyl halides of the formula (IX) are compounds generally known in organic chemistry.

Possible diluents for carrying out process (a) of the invention are inert organic solvents. Particular examples are aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoramide or esters, such as methyl acetate or ethyl acetate.

Process (a) of the invention is preferably carried out in the presence of a suitable reaction aid. All usual inorganic or organic bases are suitable for this, examples being alkaline earth or alkali metal hydroxides, such as sodium hydroxide, calcium hydroxide, potassium hydroxide or even ammonium hydroxide, alkali metal carbonates, such as sodium carbonate, potassium carbonate, potassium hydrogen carbonate, sodium hydrogen carbonate or ammonium carbonate, alkali or alkaline earth metal acetates, such as sodium acetate, potassium acetate, calciumacetate or ammonium acetate, and tertiary amines, such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

In carrying out process (a) of the invention, the reaction temperatures can be varied within a relatively wide range. Working temperatures are generally between 0° C. and +180° C., preferably between +20° C. and +120° C.

Process (a) of the invention is normally carried out at atmospheric pressure. It is nevertheless also possible to work at increased or reduced pressure.

To carry out process (a) of the invention, generally from 1.0 to 3.0 mol, preferably from 1.0 to 1.5 mol of halogenobenzene derivative of the formula (III) and optionally from 1.0 to 3.0 mol, preferably from 1.0 to 1.5 mol of base as reaction aid are used per mole of 1H-triazolinone of the formula (II). The reaction procedure, workup and isolation of the reaction products is carried out by generally usual, known processes.

Suitable diluents for carrying out process (b) of the invention are inert organic solvents. Preferred solvents are those listed in the description of carrying out process (a) of the invention.

Process (b) of the invention is preferably carried out in the presence of a suitable reaction aid. All usual inorganic or organic bases are suitable for this, examples being alkaline earth or alkali metal hydrides, hydroxides, amides, alkoxides, acetates, carbonates or hydrogen carbonates, such as, for example, sodium hydride, sodium amide, sodium methoxide, sodium ethoxide, potassium tert.-butoxide, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and tertiaryamines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

In carrying out process (b) of the invention, the reaction temperatures can be varied within a relatively wide range. Working temperatures are generally between −20° C. and +150° C., preferably between 0° C. and +120° C.

Process (b) of the invention is normally carried out at atmospheric pressure. It is nevertheless also possible to work at increased or reduced pressure.

To carry out process (b) of the invention, generally from 1.0 to 3.0 mol, preferably from 1.0 to 1.5 mol of sulphonamide of the formula (V) and optionally from 0.1 to 3.0 mol, preferably from 1.0 to 1.5 mol of base as reaction aid are used per mole of substituted triazolinone of the formula (IV).

The reaction procedure, workup and isolation of the reaction products is carried out by generally usual, known processes (cf. also the preparation examples in this respect).

Process (c) of the invention is usually carried out in the presence of a suitable acid, in particular an aqueous mineral acid. Particular preference is given to using dilute hydrochloric acid.

Possible diluents for carrying out process (c) of the invention are all the usual diluents for such diazotization reactions. Particular preference is given to using the aqueous mineral acids used as reagents, such as, for example, hydrochloric acid in corresponding excess simultaneously as diluent.

In carrying out process (c) of the invention, the reaction temperatures can be varied within a relatively wide range. Working temperatures are generally between −20° C. and +100° C., preferably between −10° C. and +80° C.

Process (c) of the invention is normally carried out at atmospheric pressure. It is nevertheless also possible to work at increased or reduced pressure.

To carry out process (c) of the invention, generally from 1.0 to 3.0 mol, preferably from 1.0 to 2.0 mol of sodium nitrite and from 1.0 to 10.0 mol, preferably from 1.0 to 5.0 mol of acid are used per mole of substituted triazolinone of the formula (Ia).

The reaction procedure, workup and isolation of the reaction products is carried out by generally usual, known processes.

Possible diluents for carrying out processes (d) and (e) of the invention are inert organic solvents. Particular examples are aliphatic, alicyclic oraromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoramide; esters, such as methyl acetate or ethyl acetate or sulphoxides, such as dimethyl sulphoxide.

Processes (d) and (e) of the invention may also optionally be carried out in a two-phase system, such as for example water/toluene or water/dichloromethane, optionally in the presence of a suitable phase transfer catalyst. Examples of such catalysts which may be mentioned are: tetrabutylammoniumiodide, tetrabutylammonium bromide, tetrabutylammonium chloride, tributylmethylphosphonium bromide, trimethyl-$C_{13}/C_{15}$-alkylammonium chloride, trimethyl-$C_{13}/C_{15}$-alkylammonium bromide, dibenzyldimethyl-ammonium methylsulphate, dimethyl-$C_{12}/C_{14}$-alkyl-benzylammonium chloride, dimethyl-$C_{12}/C_{14}$-alkyl-benzylammonium bromide, tetrabutylammonium hydroxide, triethylbenzylammonium chloride, methyltrioctylammoniumchloride, trimethylbenzylammoniumchloride, 15-crown-5, 18-crown-6 or tris-[2-(2-methoxyethoxy)-ethyl]-amine.

Processes (d) and (e) of the invention are preferably carried out in the presence of a suitable reaction aid. All usual inorganic or organic bases are suitable for this, examples being alkaline earth or alkali metal hydrides, hydroxides, amides, alkoxides, acetates, carbonates or hydrogen carbonates, such as, for example, sodium hydride, sodium amide, sodium methoxide, sodium ethoxide, potassium tert.-butoxide, sodium hydroxide, potassium hydroxide, ammonium hydroxide, sodium acetate, potassium acetate, calcium acetate, ammonium acetate, sodium carbonate, potassiumcarbonate, potassiumhydrogen carbonate, sodium hydrogen carbonate or ammonium carbonate, and tertiary a mines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

In carrying out processes (d) and (e) of the invention, the reaction temperatures can be varied within a relatively wide range. Working temperatures are generally between −20° C. and +150° C., preferably between 0° C. and 120° C.

The processes (d) and (e) of the invention is normally carried out at atmospheric pressure. It is nevertheless also possible to work at increased or reduced pressure.

To carry out process (d) of the invention, generally from 1.0 to 3.0 mol, preferably from 1.0 to 2.0 mol of alkylating agent of the formula (VI) and optionally from 1.0 to 3.0 mol, preferably from 1.0 to 2.0 mol of base as reaction aid are used per mole of substituted triazolinone of the formula (Ib).

To carry out process (e) of the invention, generally from 1.0 to 3.0 mol, preferably from 1.0 to 2.0 mol of alkylating agent of the formula (VII) and optionally from 1.0 to 3.0 mol, preferably from 1.0 to 2.0 mol of base as reaction aid are used per mole of substituted triazolinone of the formula (Ic).

The reaction procedure, workup and isolation of the reaction products is carried out in both cases by generally usual, known processes.

Possible diluents for carrying out process (f) of the invention are inert organic solvents. Particular examples are aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoramide or esters, such as methyl acetate or ethyl acetate.

Process (f) of the invention is preferably carried out in the presence of a suitable reaction aid. All usual inorganic or organic bases are suitable for this, examples being alkaline earth or alkali metal hydroxides, such as sodium hydroxide, calcium hydroxide, potassium hydroxide or even ammonium hydroxide, alkali metal carbonates, such as sodium carbonate, potassium carbonate, potassium hydrogen carbonate, sodium hydrogen carbonate or ammonium carbonate, alkali or alkaline earth metal acetates, such as sodium acetate, potassium acetate, calciumacetate or ammonium acetate, and tertiary amines, such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

To carry out process (f) of the invention, the reaction temperatures can be varied within a relatively wide range. Working temperatures are generally between 0° C. and 180° C., preferably between +20° C. and +120° C.

Process (f) of the invention is normally carried out at atmospheric pressure. It is nevertheless also possible to work at increased or reduced pressure.

To carry out process (f) of the invention, generally from 1.0 to 3.0 mol, preferably from 1.0 to 1.5 mol of sulphonyl halide of the formula (IX) and optionally from 1.0 to 3.0 mol, preferably from 1.0 to 1.5 mol of base as reaction aid are used per mole of substituted triazolinone of the formula (VIII). The reaction procedure, workup and isolation of the reaction products is carried out by generally usual, known processes.

The purification of the end products of the formula (I) is carried out by means of usual processes, for example by column chromatography or by recrystallization.

Characterization is carried out by means of the melting point or, in the case of compounds which do not crystallize, by means of proton nuclear magnetic resonance spectroscopy ($^1$H—NMR).

The active compounds of the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds of the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledon weeds of the genera: Echinochloa, Setaria, Panicum, Digitaria, Phleum, Poa, Festuca, Eleusine, Brachiaria, Lolium, Bromus, Arena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledon cultures of the genera: Oryza, Zea, Triticum, Hordeum, Arena, Secale, Sorghum, Panicum, Saccharum, Ananas, Asparagus, Allium.

However, the use of the active compounds of the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Here the active compounds of the invention can be used with particularly good results for combating dicotyledon weeds.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and tin.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl and tribenuron-methyl; thiocarbamates such as, for example, burylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying; atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1:

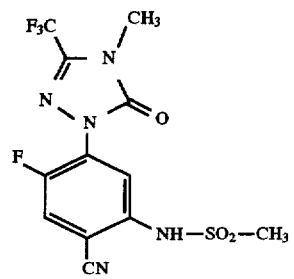

(Process b)

0.83 g (0.006 mol) of potassium carbonate are added to 1.52.g (0.005 mol) of 1-(4-cyano-2,5-difluorophenyl)-4-methyl-3-trifluoromethyl-1,2,4-triazolin-5-one and 0.48 g (0.005 mol) of methanesulphonamide in 50 ml of dimethyl sulphoxide at room temperature, and the mixture is subsequently heated for 12 hours at 120° C. Workup is by adding the cooled reaction mixture to water, adjusting the pH to 2 using dilute hydrochloric acid and extracting a number of times with dichloromethane. The combined organic phases are dried over sodium sulphate and concentrated in vacuo. The residue is chromatographed on silica gel (eluent: dichloromethane/methanol 20:1).

0.55 g (28% of theory) of 1-(4-cyano-2-fluoro-5-methyl-sulphonylamino-phenyl)-4-methyl-3-trifluoromethyl-1,2,4-triazolin-5-one is obtained, having a melting point of 67° C.
Preparation of the starting compounds:

Example IV-1:

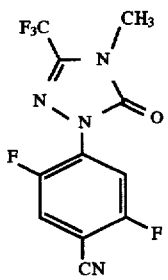

5.8 g (0.042 mol) of potassium carbonate are added to 6.3 g (0.034 mol) of 4-methyl-3-trifluoromethyl-1,2,4-5 triazolin-5-one (cf. for example U.S. Pat. No. 3,780,052) and 5.4 g (0.034 mol) of 2,4,5-trifluorobenzonitrile (cf. for example EP 191181) in 150 ml of dimethyl sulphoxide at room temperature, and the mixture is subsequently heated for1 14 hours at 100° C. Workup is by adding the cooled reaction mixture to water, adjusting the pH to 2 using dilute hydrochloric acid and extracting a number of times with dichloromethane. The combined organic phases are dried over sodiumsulphate and concentrated in vacuo. The residue is chromatographed on silica gel (eluent: dichloromethane).

6.2 g (60% of theory) of 1-(4-cyano-2,5-difluorophenyl)-4-methyl-3-trifluoromethyl-1,2,4-triazolin-5-one are obtained, having a melting point of 74° C.

Example X-1:

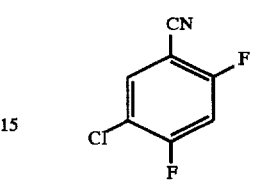

220 g (1.06 mol) of 2,4,5-trichlorobenzonitrile (cf. for example EP 441 004) are added to 250 g (4.31 mol) of potassium fluoride in 400 ml of distilled tetramethylene sulphone while stirring at room temperature, and the mixture is subsequently stirred for 10 hours at from 195° C. to 200° C. Workup is by cooling, adding 500 ml of water and steam-distilling the mixture. The organic portion is taken up in dichloromethane, dried over sodium sulphate, concentrated in vacuo and distilled.

108 g (58% of theory) of 2,4-difluoro-5-chlorobenzonitrile are obtained, having a boiling point of 105°–107° C. at 30 mbar and a melting point of 48°–50° C.

The following substituted triazolinones of the general formula (I) are obtained in a corresponding way and according to the general preparation instructions:

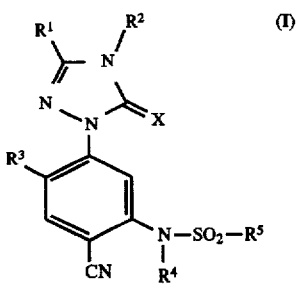

| Example no. | 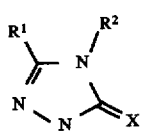 | R³ | R⁴ | R⁵ | Physical properties |
|---|---|---|---|---|---|
| 2 | H₃C, OCH₃ structure | F | H | n-C₄H₉ | m.p. 128° C. |

-continued
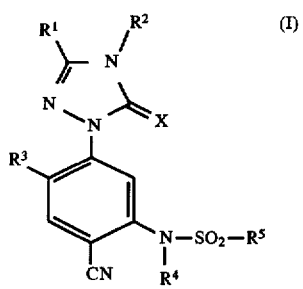
| | | R³ | | | |
|---|---|---|---|---|---|
| 3 | 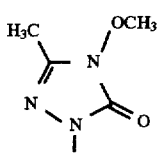 | Cl | H | CH₃ | m.p. 81° C. |
| 4 | 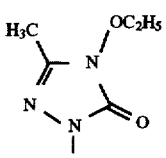 | Cl | H | CH₃ | m.p. 155° C. |
| 5 | 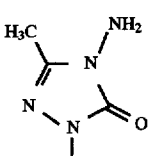 | F | H | n-C₄H₉ | m.p. 69° C. |
| 6 | 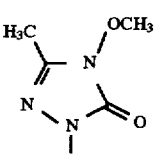 | F | H | C₆H₅ | m.p. 193° C. |
| 7 | 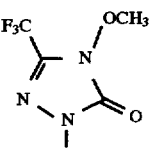 | F | H | CH₃ | m.p. 178° C. |
| 8 | 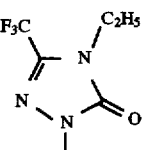 | F | H | C₂H₅ | ¹H-NMR*): 1.4–1.48; 3.2–3.2; 3.9–3.98 |
| 9 | 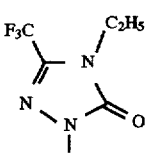 | F | H | CH₃ | ¹H-NMR*): 3.15; 3.9–3.98; 7.5–7.55 |

-continued
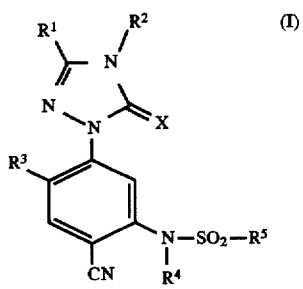
| No. | R¹/R² group | R³ | R⁴ | R⁵ | Data |
|---|---|---|---|---|---|
| 10 | F₃C-, cyclopropyl (triazolinone) | F | H | CH₃ | ¹H-NMR*): 1.15–1.25; 2.95–3.05; 3.17; 7.6 |
| 11 | F₃C-, C₂H₅ (triazolinone) | F | CH₃ | CH₃ | m.p. 128° C. |
| 12 | F₃C-, C₂H₅ (triazolinone) | Cl | H | CH₃ | m.p. 111° C. |
| 13 | F₃C-, CH₂-CH=CH₂ (triazolinone) | F | H | CH₃ | ¹H-NMR*): 3.19; 4.47–4.5; 7.52–7.55 |
| 14 | H₃C-, CHF₂ (triazolinone) | F | H | CH₃ | m.p. 87° C. |
| 15 | H₃C-, OC₂H₅ (triazolinone) | F | H | CH₃ | m.p. 180° C. |
| 16 | F₃C-, C₂H₅ (triazolinone) | F | H | 2,4,6-trimethylphenyl | m.p. 162–163° C. |

-continued
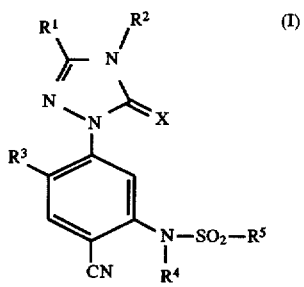
| | R¹, R² | R³ | | R⁵ | |
|---|---|---|---|---|---|
| 17 | 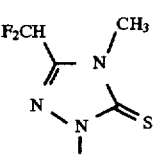 | F | H | CH₃ | m.p. 169–170° C. |
| 18 | 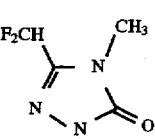 | F | H | CH₃ | m.p. 203–204° C. |
| 19 | 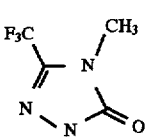 | F | H | CH₃ | m.p. 159° C. |
| 20 | 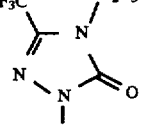 | F | H | 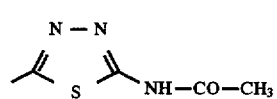 | m.p. >250° C. |
| 21 | 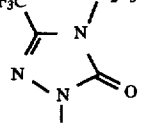 | F | H | n-C₈H₁₇ | m.p. 78–79° C. |
| 22 | 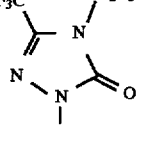 | F | H | n-C₄H₉ | m.p. 111–112° C. |
| 23 | 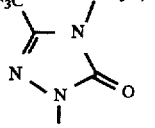 | F | H | CH₃ | m.p. 149° C. |

-continued
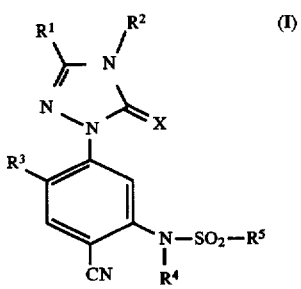
| | | R³ | R⁴ | R⁵ | |
|---|---|---|---|---|---|
| 24 | H₃C-/NH₂ triazolinone (CH₃ N-ring) | F | H | CH₃ | m.p. 117–119° C. |
| 25 | H₃C-/OCH₃ triazolinone | H | H | CH₃ | m.p. 210° C. |
| 26 | F₃C-/CH₃ triazolinone | F | H | C₂H₅ | ¹H-NMR*): 1.45; 2.18; 3.25; 3.5; 7.23; 7.52; 8.01 |
| 27 | F₃C-/CH₃ triazolinone | F | H | C₆H₅ | m.p. 79° C. |
| 28 | F₃C-/C₂H₅ triazolinone | F | H | CH₃ | m.p. >250° C. |
| 29 | H₃C-/NH₂ triazolinone | Cl | H | CH₃ | m.p. 97° C. |
| 30 | F₃C-/C₂H₅ triazolinone | F | C₂H₅ | CH₃ | m.p. 131–133° C. |

-continued

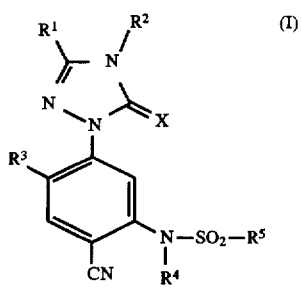

| | | R³ | | R⁴ R² R⁵ | |
|---|---|---|---|---|---|
| 31 | F₃C, C₂H₅ triazolinone (X=O) | F | H | i-C₃H₇ | ¹H-NMR*): 1,38–1,45; 3,9–3,97; 7,38–7,42 |
| 32 | F₃C, C₂H₅ triazolinone (X=O) | F | H | 5-chloro-2-thienyl-methyl | ¹H-NMR*): 3,90–3,98; 6,95; 7,45–7,50 |
| 33 | CHF₂, C₂H₅ triazolinethione (X=S) | F | H | C₂H₅ | m.p. 104–106° C. |
| 34 | F₃C, C₂H₅ triazolinone | F | C₂H₅ | C₂H₅ | sirup |
| 35 | F₃C, C₂H₅ triazolinone | F H (=triethylammonium-salt of Example 8) | | C₂H₅ | ¹H-NMR*): 2,95–3,05 3,15–3,25; 7,92–7,95 |
| 36 | F₃C, C₂H₅ triazolinone | F H (=potassium salt of Example 8) | | C₂H₅ | m.p. >260° C. |
| 37 | F₃C, C₂H₅ triazolinone | F H (=isopropylammonium-salt of Example 8) | | C₂H₅ | m.p. 58–60° C. |

-continued

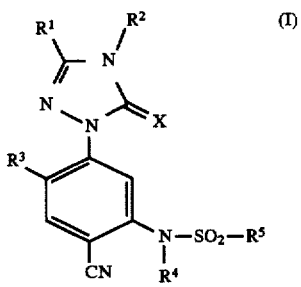

| | R¹, R² | R³ H | R⁵ | m.p. |
|---|---|---|---|---|
| 38 | F₃C / C₂H₅ triazolinone (N-CH₃) | F H (=ammonium salt of Example 8) | C₂H₅ | m.p. 63–64° C. |
| 39 | F₃C / C₂H₅ triazolinone (N-CH₃) | F H | 2-methylphenyl-oxadiazole (3-methyl-1,2,4-oxadiazol-5-yl) | m.p. 137–139° C. |
| 40 | CHF₂ / C₂H₅ triazolinone (N-CH₃) | F H | C₂H₅ | m.p. 131–133° C. |
| 41 | CHF₂ / CH₃ triazolinone (N-CH₃) | F H | C₂H₅ | m.p. 157–159° C. |
| 42 | CHF₂ / CH₃ triazoline-thione (N-CH₃) | F H | C₂H₅ | m.p 178–180° C. |
| 43 | CHF₂ / CH₂ triazoline-thione (N-CH₃) | F H | i-C₃H₇ | m.p. 184–185° C. |
| 44 | F₃C / C₂H₅ triazoline-thione (N-CH₃) | F H | C₂H₅ | m.p. 126–128° C. |

-continued
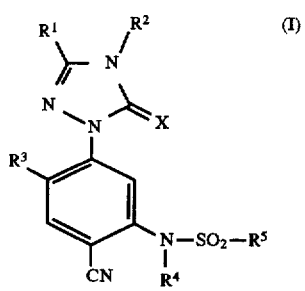
| | | R³ | SO₂—R⁵ | R⁴ | |
|---|---|---|---|---|---|
| 45 | 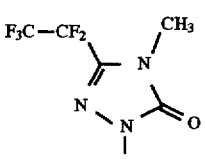 | F | SO₂CH₃ | C₂H₅ | m.p. 166–168° C. |
| 46 | 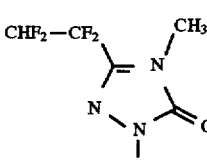 | F | H | C₂H₅ | m.p. 151–153° C. |
| 47 | 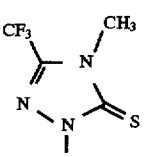 | F | H | C₂H₅ | m.p. 170–172° C. |
| 48 | 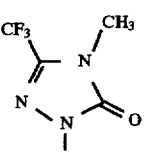 | H | H | CH₃ | m.p. 165° C. |
| 49 | 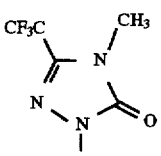 | Cl | H | CH₃ | wax |
| 50 | 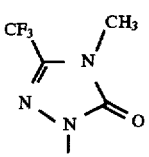 | F | H | i-C₃H₇ | m.p. 34° C. |
| 51 | | F | H | nC₃H₇ | m.p. 108° C. |

-continued
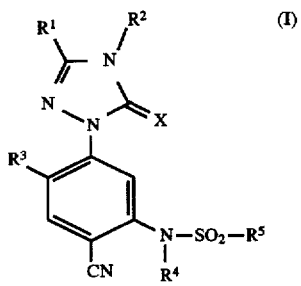
| | | R³ | R⁴ | R⁵ | |
|---|---|---|---|---|---|
| 52 | 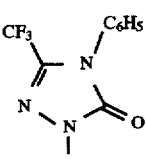 | F | H | C₂H₅ | m.p. 52° C. |
| 53 | 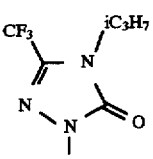 | H | H | CH₃ | m.p. 190° C. |
| 54 | 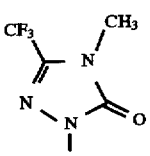 | H | H | CH₃ | m.p. 173° C. |
| 55 | 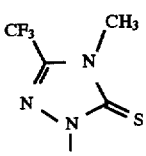 | Cl | H | CH₃ | m.p. 158° C. |
| 56 | 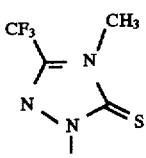 | F | H | C₆H₅ | wax |
| 57 | 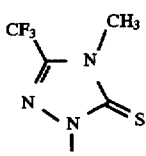 | F | H | i-C₃H₇ | m.p. 27° C. |
| 58 | 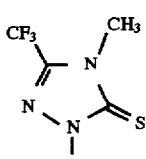 | F | H | n-C₃H₇ | m.p. 29° C. |

-continued
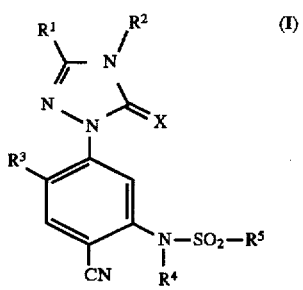
| | | R³ | R⁴ | R⁵ | |
|---|---|---|---|---|---|
| 59 | 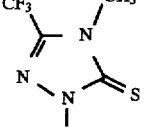 | F | H | C₂H₅ | m.p. 176° C. |
| 60 | 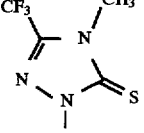 | F | C₂H₅ | C₂H₅ | m.p. 144° C. |
| 61 | 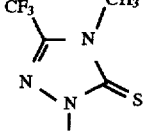 | F | H | CH₂—C₆H₅ | m.p. 111° C. |
| 62 | 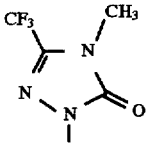 | F | H | CH₂—C₆H₅ | m.p. 103° C. |
| 63 | 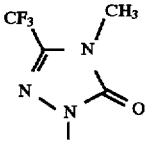 | F | CH₃ | CH₃ | m.p. 34° C. |
| 64 | 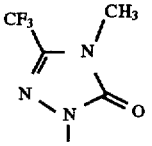 | F | CH₃ | C₂H₅ | m.p. 43° C. |
| 65 | 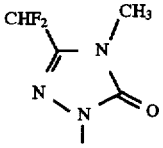 | F | H | C₂H₅ | m.p. 100° C. |

-continued
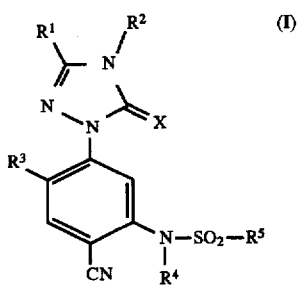
| | R¹ | R² | R³ | R⁴ | R⁵ | |
|---|---|---|---|---|---|---|
| 66 | CHF₂, N-CH₃ triazolinone (N-CH₃, =O) | | Cl | H | C₂H₅ | m.p. 63° C. |
| 67 | CHF₂, N-CH₃ triazolinone (N-CH₃, =O) | | Cl | H | n-C₄H₉ | oil |
| 68 | CHF₂, N-CH₃ triazolinone (N-CH₃, =O) | | Cl | H | n-C₈H₁₇ | oil |
| 69 | CHF₂, N-CH₃ triazolinone (N-CH₃, =O) | | Cl | H | CH₃ | m.p. 96–98° C. |
| 70 | H₃C, NH triazoline (N-CH₃) 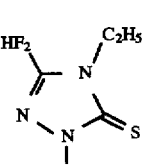 | | F | H | CH₃ | wax |
| 71 | CF₂, N-C₂H₅ triazolinone (N-CH₃, =O) | | F | C₂H₅ | C₂H₅ | ¹H-NMR*⁾: 3,20–3,28; 3,80–3,88–3,90–3,98 |
| 72 | CHF₂, N-C₂H₅ triazolinethione (N-CH₃, =S) | | F | H | CH₃ | m.p. 192–194° C. |

-continued
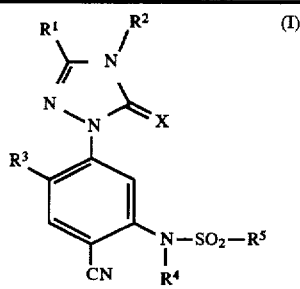
| Example No. | R¹ / ring | R³ | R⁴ | R⁵ | Physical properties |
|---|---|---|---|---|---|
| 73 | CF₂, CH₃, N-N(CH₃), S (triazole-thione) | F | H | (2-thienyl) | m.p. 47° C. |
| 74 | CHF₂, C₂H₅, N-N(CH₃), O | F | H | CH₃ | m.p. 211–213° C. |
| 75 | CHF₂-CF₂, CH₃, N-N(CH₃), O | F | H | C₂H₅ | Smp. 129–131° C. |
| 76 | CF₃, CH₃, N-N(CH₃), S | F | CH₃ | C₂H₅ | Smp. 131° C. |
| 77 | CF₃, CH₃, N-N(CH₃), O | F | H | (2-thienyl) | m.p. 48° C. |
| 78 | CF₃CH₂O, CH₃, N-N(CH₃), O | F | H | CH₃ | m.p. 144° C. |
| 79 | F₂CH, CH₃, N-N(CH₃), O | F | SO₂CH₃ | CH₃ | m.p. 261–263° C. |

-continued
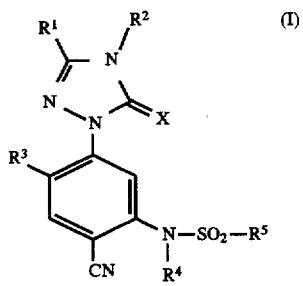
| | R¹ R² (ring) | R³ | R⁵ | R⁴ | m.p. |
|---|---|---|---|---|---|
| 80 | F₂CH, N-CH₃, N-N-CH₃, C=O | F | SO₂CH₃ | C₂H₅ | m.p. 196–198° C. |
| 81 | F₂CH, N-C₂H₅, N-N-CH₃, C=S | F | SO₂CH₃ | CH₃ | m.p. 195–197° C. |
| 82 | F₂CH, N-C₂H₅, N-N-CH₃, C=S | F | SO₂CH₃ | C₂H₅ | m.p. 202–204° C. |
| 83 | F₃C, N-C₂H₅, N-N-CH₃, C=O | F | SO₂C₂H₅ | C₂H₅ | m.p. 132–134° C. |
| 84 | F₃C, N-C₂H₅, N-N-CH₃, C=O | F | CH₃ | C₂H₅ | m.p. 109–111° C. |
| 85 | F₃C, N-C₂H₅, N-N-CH₃, C=O | F | i-C₃H₇ | C₂H₅ | m.p. 137–139° C. |
| 86 | F₃C, N-C₂H₅, N-N-CH₃, C=O | F | CH₂COOC₂H₅ | C₂H₅ | m.p. 122–124° C. |
| 87 | H₃C, N-OCH₂C₆H₅, N-N-CHF-, C=O | F | H | C₂H₅ | m.p. 160–162° C. |

-continued

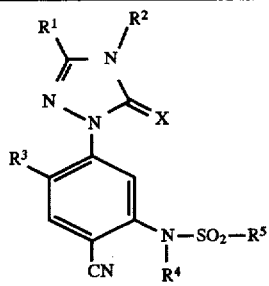

| | | X | R³ | R⁴ | R⁵ | |
|---|---|---|---|---|---|---|
| 88 | F₃C─⟨triazole⟩─CH₃ (N-CH₃) | O | F | SO₂CH₃ | CH₃ | m.p. 168° C. |
| 89 | F₃CH─⟨triazole⟩─CH₃ (N-CH₃) | S | F | SO₂CH₃ | C₂H₅ | m.p. 171-173° C. |

*)The ¹H-NMR spectra were recorded in deuterochloroform (CDCl₃) using tetramethylsilane (TMS) as internal standard. The indicated value is the chemical shift δ in ppm.

Application examples:

In the following application example, the compound below was used as comparative substance:

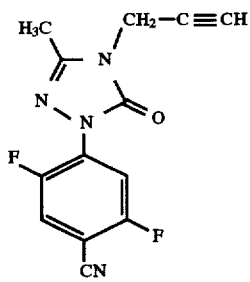

3-Methyl-4-propargyl-1-(2,5-difluoro-4-cyano-phenyl)-1,2,4-triazolin-5-one
(known from DE 38 39 480)

Example A

Pre-emergence test
Solvent: 5 parts by weight of acetone
Emulsifier: 1 part by weight of alkylaryl polyglycol ether To produce a suitable preparation of active compound, one part by weight of active compound is mixed with the stated amount of solvent, the stated mount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, the compounds according to Preparation Examples 3 and 8 exhibit significantly superior activity in comparison with the prior art. These compounds show an activity of from 80 to 100% at application rates of from 50 to 500 g/ha against problem weeds such as Abuthilon, Cassia, Chenopodium, Galinsoga, Matricaria and Portulaca whereas the prior art, in the form of compound (A) from DE 3 839 480, at an application rate of 500 g/ha mostly shows no herbicidal activity at all and only 70% for Galinsoga and 20% for Matricaria.

It will be understood that the specification and examples are illustrative but not limitative of the present invention and that other embodiments within the spirit and scope of the invention will suggest themselves to those skilled in the art.

What is claimed is:

1. A substituted triazolinone of the formula

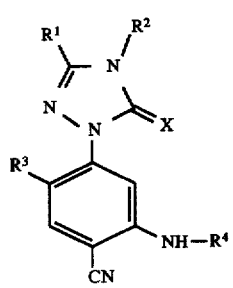

wherein $R^1$ represents hydrogen, fluorine, chlorine, bromine, iodine, cyano, hydroxyl or one of the radicals —$R^6$, —O—$R^6$, —O—$NR^6R^7$, —S—$R^6$, —S(O)—$R^6$ or —$SO_2$—$R^6$, $R^2$ represents hydrogen, hydroxyl, amino, cyano or one of the radicals —$R^6$, —O—$R^6$ or —N=$CR^6R^7$, $R^3$ represents hydrogen, fluorine, chlorine, bromine, iodine, a straight chain or branched alkyl having from 1 to 8 carbon atoms or a straight chain or branched halogenoalkyl having from 1 to 8 carbon atoms and from 1 to 17 halogen atoms which may be identical or different, $R^4$ represents hydrogen, one of the radicals —$R^6$, —O—$R^6$ or —$SO_2$—$R^6$, one equivalent of an alkali metal or alkaline earth metal cation, or an ammonium cation which is optionally singly or multiply substituted by alkyl(s) having from 1 to 16 carbon atoms and which are identical or different, and X represents oxygen or sulphur, where $R^6$ represents straight chain or branched alkyl having from 1 to 14 carbon atoms and which is optionally singly or multiply substituted wherein the substituents are selected from the group consisting of halogen, cyano, carboxyl, carbamoyl, alkoxy, alkoxyalkoxy, alkylthio, alkylsulphinyl, alkylsulphonyl, alkoxycarbonyl, N-alkylaminocarbonyl, N,N-dialkylaminocarbonyl, trialkylsilyl and alkylsulphonylaminocarbonyl wherein said alkyl moieties are straight chain or branched and each have from 1 to 8 carbon atoms; or $R^6$ represents alkenyl or alkinyl each having from 2 to 8 carbon atoms and which are optionally singly or multiply substituted by halogen which may be identical or different; or $R^6$ represents cycloalkyl having from 3 to 7 carbon atoms and which is optionally singly or multiply substituted by halogen which is identical or different or straight chain or branched alkyl having from 1 to 4 carbon atoms; or $R^6$ also represents arylalkyl or aryl each having from 6 to 10 carbon atoms in the aryl part and optionally from 1 to 4 carbon atoms in the straight chain or branched alkyl part and which are optionally singly or multiply substituted in the aryl part by substituents which are identical or different and the substituents are halogen, cyano, nitro, amino, N-acetylamino, or alkyl, alkoxy, alkylthio, alkylsulphinyl or alkylsulphonyl which are straight chain or branched and each have from 1 to 6 carbon atoms, halogenoalkyl, halogenoalkoxy, halogenoalkylthio, halogenoalkylsulphinyl or halogenoalkylsulphonyl which are straight chain or branched and each have 1 to 6 carbon atoms and from 1 to 13 halogen atoms which may be identical or different, alkoxycarbonyl or alkoximinoalkyl which are straight chain or branched and each have from 1 to 6 carbon atoms in the individual alkyl parts and optionally substituted phenyl wherein the substituents are identical or different and are selected from the group consisting of halogen, straight chain or branched alkyl, straight chain or branched halogenoalkyl and halogenoalkoxy wherein said alkyl moieties have 1 to 6 carbon atoms;

$R^7$ represents hydrogen or straight chain or branched alkyl having from 1 to 8 carbon atoms and which is optionally singly or multiply substituted wherein the substituents are halogen, cyano, carboxyl, carbamoyl, or alkoxy, alkoxyalkoxy, alkylthio, alkylsulphinyl, alkylsulphonyl, alkoxycarbonyl, N-alkylaminocarbonyl, N,N-dialkylaminocarbonyl, trialkylsilyl or alkylsulphonylaminocarbonyl which are straight chain or branched and each have from 1 to 8 carbon atoms in the individual alkyl moieties; or $R^7$ represents alkenyl or alkinyl each having from 2 to 8 carbon atoms and which are optionally singly or multiply substituted by halogen which may be identical or different; or $R^7$ represents cycloalkyl having from 3 to 7 carbon atoms and which is optionally singly or multiply substituted by halogen or straight chain or branched alkyl having from 1 to 4 carbon atoms; or $R^7$ represents arylalkyl or aryl each having from 6 to 10 carbon atoms in the aryl part and optionally from 1 to 4 carbon atoms in the straight chain or branched alkyl part and which are optionally singly or multiply substituted in the aryl part wherein the substituents are halogen, cyano, nitro, or alkyl, alkoxy, alkylthio, alkylsulphinyl or alkylsulphonyl which are straight chain or branched and each have from 1 to 6 carbon atoms, halogenoalkyl, halogenoalkoxy, halogenoalkylthio, halogenoalkylsulphinyl or halogenoalkylsulphonyl which are each straight chain orbranched and each have from 1 to 6 carbon atoms and from 1 to 13 halogen atoms which are identical or different, alkoxycarbonyl or alkoximinoalkyl which are straight chain or branched and each have from 1 to 6 carbon atoms in the individual alkyl parts and optionally substituted phenyl wherein the substituents are identical or different and are halogen, straight chain or branched alkyl or alkoxy, having straight chain or branched halogenoalkyl or halogenoalkoxy wherein said alkyl moieties have 1 to 6 carbon atoms.

2. A substituted triazolinone according to claim 1, wherein $R^1$ is hydrogen.

3. A triazolinone according to claim 1, of the formula

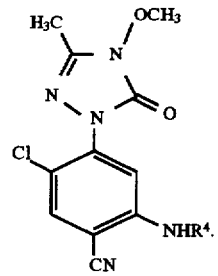

4. A substituted triazolinone according to claim 1, of the formula

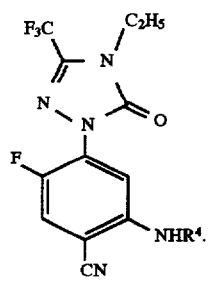

5. A substituted triazolinone according to claim 1, of the formula

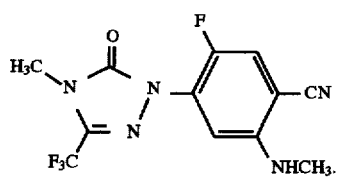

* * * * *

UNITED STATES PATENT AND TRADEMARK OFFICE
CERTIFICATE OF CORRECTION

PATENT NO. : 5,663,362
DATED : September 2, 1997
INVENTOR(S) : Haas, et al.

It is certified that error appears in the above-indentified patent and that said Letters Patent is hereby corrected as shown below:

Title Page [*] Notice: Line 3 delete " 5,378,687 and substitute -- 5,378,681 --

Title Page ABSTRACT: Line 12 delete " -SO-$R^6$ " and substitute -- -$SO_2$-$R^6$ --

Signed and Sealed this

Eleventh Day of November, 1997

Attest:

BRUCE LEHMAN

Attesting Officer

Commissioner of Patents and Trademarks